United States Patent [19]
Tuy

[11] Patent Number: 5,625,660
[45] Date of Patent: Apr. 29, 1997

[54] IMAGE RECONSTRUCTION FROM HELICAL PARTIAL CONE-BEAM DATA

[75] Inventor: Heang K. Tuy, Chesterland, Ohio

[73] Assignee: Picker International, Inc., Highland Heights, Ohio

[21] Appl. No.: 497,296

[22] Filed: Jun. 30, 1995

[51] Int. Cl.$^6$ .................................................. A61B 6/03
[52] U.S. Cl. .............................................. 378/15; 378/901
[58] Field of Search .................. 364/413.16, 413.17, 364/413.21, 413.24; 378/15, 901; 250/363.04

[56] References Cited

U.S. PATENT DOCUMENTS

| | | | |
|---|---|---|---|
| 5,210,421 | 5/1993 | Gullberg et al. | 250/363.4 |
| 5,337,231 | 8/1994 | Nowak et al. | 364/412.24 |
| 5,377,250 | 12/1994 | Hu | 378/15 |
| 5,396,528 | 3/1995 | Hu et al. | 364/413.16 |
| 5,400,377 | 3/1995 | Hu et al. | 378/8 |
| 5,404,293 | 4/1995 | Weng et al. | 364/413.19 |

OTHER PUBLICATIONS

"An Inversion Formula for Cone-Beam Reconstruction", Tuy, SIAM J. Appl. Math vol. 43, No. 3, Jun. 1983 pp. 546–552.

"A Cone-Beam Reconstruction Algorithm Using Shift-Variant Filtering and Cone-Beam Backprojection", Defrise, et al. IEEE Trans. on Med. Imaging, vol. 13, No. 1, Mar. 1994 pp. 186–195.

"Mathematical Framework of Cone Beam 3D Reconstruciton Via the First Derivative of the Radon Transform", Grangeat, Mathematical Methods in Tomography, Proceedings from Conference of Oberwolfach, Germany Jun. 1990.

"Derivation and Implementation of a Cone-Beam Reconstruction Algorihm for Nonplanar Orbits", Kudo, IEEE Transations on Med. Imaging, vol. 13, No. 1 1994, pp. 196–211 no month.

"An Extended Completeness Condition for Exact Cone-Beam Reconstruction and Its Application", Kudo, 1994 IEEE Conference on Medical Imaging no month.

"Implementation of Tuy's Cone-Beam Inversion Formula", Zeng, et al. Phys. Med. Biol. 39 (1994) 493–507 no month.

*Primary Examiner*—David P. Porta
*Assistant Examiner*—David Vernon Bruce
*Attorney, Agent, or Firm*—Fay, Sharpe, Beall, Fagan, Minnich & McKee

[57] ABSTRACT

A two-dimensional radiation detector (30) receives divergent ray penetrating radiation along conical or pyramidal ray paths which converge at an apex. The radiation may emanate from one or both of an x-ray tube (16) or radionuclei injected into a human subject. As the radiation detector rotates around the subject, it is repeatedly sampled to generate two-dimensional data sets $h_t(u,v)$ at each of a plurality of samplings t. Each two-dimensional data array is weighted (44) and divided into two components. A first component processor (48) convolves a first component of each two-dimensional array with respect to u for each v. A second component processor (50) processes a second component of each two-dimensional array (FIG. 6) including weighting each component with a geometrically dependent weighting function W from a weighting function computer (46). The processed first and second components are combined (52) and backprojected (54).

15 Claims, 14 Drawing Sheets

IMAGE RECONSTRUCTION FROM HELICAL PARTIAL CONE-BEAM DATA

BACKGROUND OF THE INVENTION

The present invention relates to the image reconstruction art. It finds particular application in conjunction with reconstructing x-ray transmission data from CT scanners which move a partial cone-beam radiation source along a helical trajectory and will be described with particular reference thereto. It is to be appreciated, however, that the present application will also find application in reconstructing information from other conical or other three-dimensional x-ray sources, such as reconstructing conical transmission or emission data in nuclear cameras.

Conventionally, spiral CT scanners include an x-ray source which projects a thin slice or beam of radiation. The x-ray source is mounted for rotational movement about a subject who is moving along the axis of rotation. An arc or ring of radiation detectors receive radiation which has traversed the patient. Data from the x-ray detectors represents a single spiralling slice through the patient. The data from the detectors is reconstructed into a three-dimensional image representation.

For faster processing, a pair or more of radiation detectors can be disposed next to each other. This enables two or more slices of data to be collected concurrently. However, like the single slice scanner, only intraslice data is used in the reconstruction process.

One of the difficulties with such prior art scanners is that they place major stress on the x-ray generator. When a solid geometric shape of x-rays, such as a cone, are generated, the x-rays pass through a volumetric region of the subject. In true cone beam reconstruction, truncation of the data is not permitted. These x-rays pass along known rays, both within traditional planes and at acute angles through several planes. The radiation passing through rays at an angle to the central plane were previously lost to collimation. By utilizing the radiation previously lost in collimation to generate useful diagnostic information, the load on the x-ray generator is reduced.

However, images reconstructed from data collected along divergent beams tend to have artifacts. One way of minimizing the divergent ray artifacts is to minimize the number of rings, i.e., limit the width of the cone beam. Of course, limiting the width of the cone-beam partially defeats the original intent.

Although the additional radiation supplied by the cone-beam is beneficial in imaging, it has the detrimental side effect of increasing patient dosage. On the other hand, the high dosage enables a volume to be constructed with fewer rotations of the cone-beam.

The present invention provides a new and improved method and apparatus for reconstructing volumetric images from cone and other three-dimensional x-ray geometries.

SUMMARY OF THE INVENTION

In accordance with the present invention, a new and improved method and apparatus for reconstructing an image from helical cone-beam data is provided. A source generates penetrating radiation about a subject. A two-dimensional radiation detector receives the radiation along a plurality of divergent rays. The rays are focused at a common origin vertex and diverge in two dimensions. The radiation detector is mounted and rotated about the subject along at least a helical arc segment of a helical path. A sampling means samples the radiation detector at a plurality of angular increments along the helical arc segment to generate a plurality of two-dimensional views. Each view includes a two-dimensional array of data values, where each data value corresponds to one of the divergent rays. Data along rows parallel to a tangent to the helix at the vertex of the cone are not truncated but data in orthogonal or other directions can be truncated. The data collected for each cone is referenced with respect to a local coordinate plane. A weighting processor weights the data values of each two-dimensional array in accordance with a cosine of an angle between a ray corresponding to the data value and a ray normal to the radiation detector or local coordinate plane. A first component processor convolves a first component of the weighted data values one-dimensionally in the direction of the tangent to create a convolved first two-dimensional data component array. A second component processor processes a second two-dimensional component array of the weighted data values. The second processor weights each second component value in accordance with characteristics of the helical arc segment and positioned along the helical arc segment. The second processor further takes a partial derivative of the data values of the second component, and multiplies each data value in accordance with a square of a distance from the vertex of the divergent rays to the radiation detector corresponding to each data value. An adder sums the first and second processed components from the first and second component processors. A three-dimensional backprojector backprojects the sum from the adder into a volumetric image memory.

In accordance with a more limited aspect of the present invention, the second component processor includes a means for computing a line integral of the weighted data, a means for computing a cosine weighted first derivative of the line integral, a means for computing a product of the cosine weighted line integral and a weighting function, a means for computing a partial-derivative of the product, a means for two-dimensionally backprojecting the partial derivative to generate a backprojection, and a means for weighting the backprojection to form the processed second two-dimensional component array.

In accordance with a more limited aspect of the invention, the weighting factor is calculated in accordance with characteristics of the helical arc segment.

In accordance with another aspect of the present invention, a method for radiographic diagnostic imaging is provided. Penetrating radiation is generated. The radiation is received with a two-dimensional radiation detector along a plurality of divergent rays. The rays are focused at a common origin vertex and diverge in two-dimensions. The radiation detector is mounted and rotated about a subject along at least a helical arc segment of a helical path. The radiation detector is sampled at a plurality of angular increments along the helical arc segment to generate a plurality of two-dimensional views. Each view includes a two-dimensional array of data values, where each data value corresponds to one of the divergent rays. The data values of each two-dimensional array is weighted in accordance with a cosine of an angle between a ray corresponding to the data value and a ray normal to the local coordinate planes. A first component of the weighted data is convolved to create a convolved first two-dimensional data component array. A second two-dimensional component array of the weighted data is processed, where each second component value is weighted in accordance with characteristics of the helical arc segment and positioned along the helical arc segment. A partial derivative of the data values of the second component is taken. Each data value is multiplied in accordance with a square of a distance from the vertex of the divergent rays to the radiation detector corresponding to each data value. The first and second processed components are then summed. The sum is then backprojected into a volumetric image memory.

One advantage of the present invention is that it provides for faster reconstruction of images of volumetric regions.

Another advantage of the present invention is that it enables volumetric images to be reconstructed with less than a full rotation of an x-ray source.

Another advantage of the present invention resides in reduced image artifacts.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figures 1A, 1B:
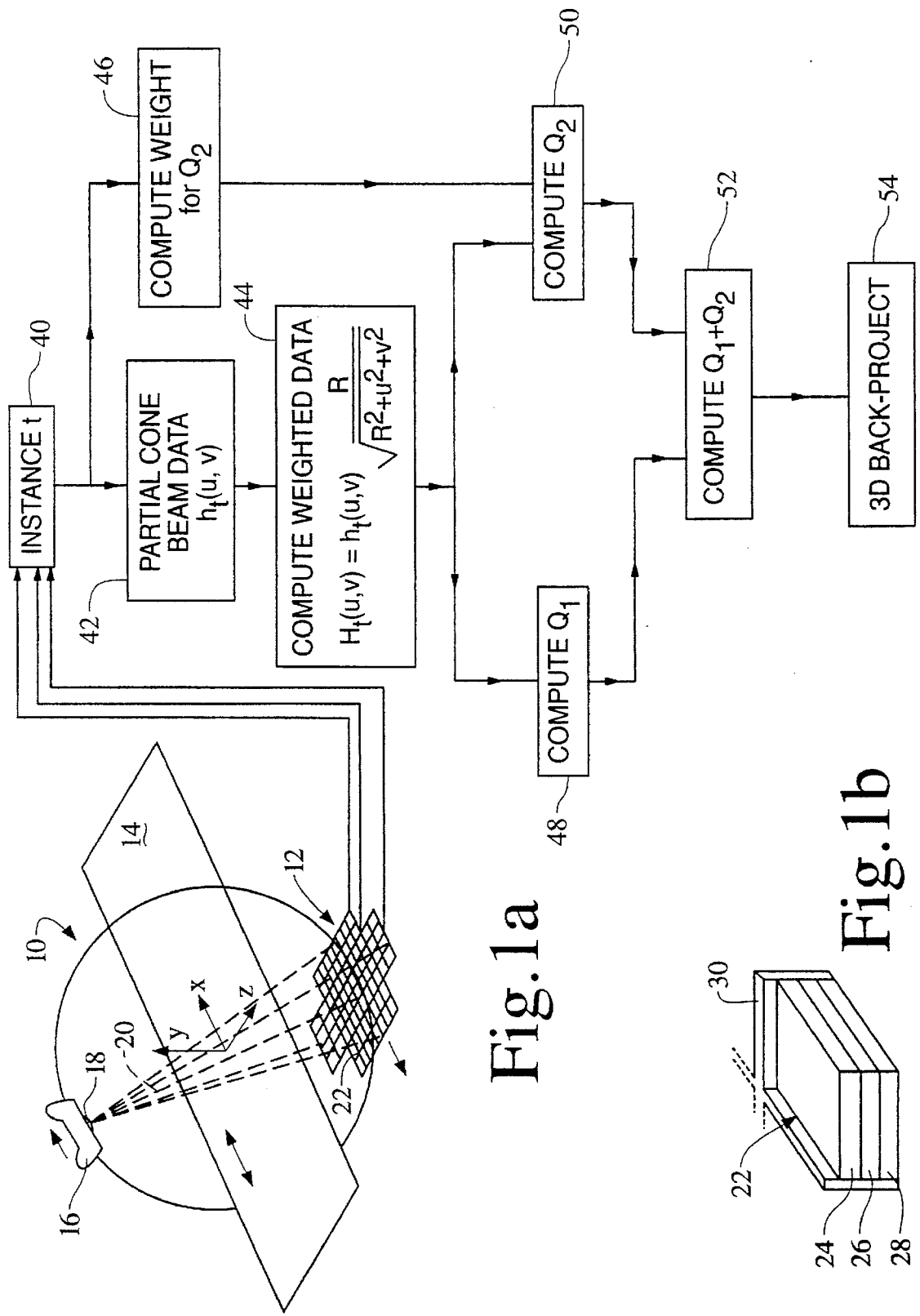
FIG. 1a is an illustration of an imaging system in accordance with the present invention.
FIG. 1b is an illustration of a detector element used in the present invention.

With reference to FIGS. 1a and 1b, a medical diagnostic imaging apparatus 10 includes an x-ray detector 12 which receives radiation arriving from a subject on a subject support 14. In the preferred CT scanner embodiment, radiation emanates from an x-ray tube 16 having radiation. The cone-beam, as defined herein, can have a circular cross-section, a square or rectangular cross-section, a hexagonal cross-section, or the like.

The radiation detector 12 of the preferred embodiment includes an array of detector elements mounted in a configuration which mimics the cross-section of the x-ray beam 20. For example, a dozen square detector elements 22 may be mounted in a pattern which approximates a circle. When the beam is rectangular or square, the detector elements would be positioned in a corresponding square or rectangular pattern. As yet another alternate embodiment, a plurality of stationary rings of the detector elements can be mounted around the subject. Providing a plurality of stationary rings of the detector elements adds cost in the detectors, but removes the cost associated with rotating the detector assembly.

Each of the detector assemblies 22 includes a scintillation crystal 24 disposed toward the radiation source, an array of photodetectors 26 disposed to view the scintillation crystal, and an array of integrated circuits 28 connected with the array of photodetectors 26. Preferably, the scintillation crystal, photodetector, and integrated circuit assembly is mounted on a common substrate. The scintillation crystal and photodetectors are etched or cut to define a larger number of light-sensitive elements, e.g., a 16×16 array. Optionally, a detector collimator 30 is mounted to the scintillation crystals to limit received radiation to radiation travelling along rays from an origin of the cone-beam collimator. In the CT scanner embodiment, the origin of the collimator is selected to match the focal point of the x-ray tube.

Alternately, the medical diagnostic apparatus may be a nuclear camera. In the nuclear camera, the radiation source includes an emission radiation source in the form of a radiopharmaceutical that is injected into the subject. Because the cone-beam collimator limits received radiation to radiation travelling along a conical array of rays, the resultant data is again cone-beam data. Further, a transmission line source may be disposed opposite the patient from the radiation detector. In a nuclear camera, the transmission line source is commonly a radioisotope.

As is known in the art, an appropriate means or mechanical mechanism is provided for rotating the radiation source and the detector around the subject and subject support. In a CT camera, the radiation source commonly rotates continuously at a relatively high rate of speed. In a nuclear camera, the detector and transmission radiation source, if any, commonly rotate in incremental steps.

Figure 2:
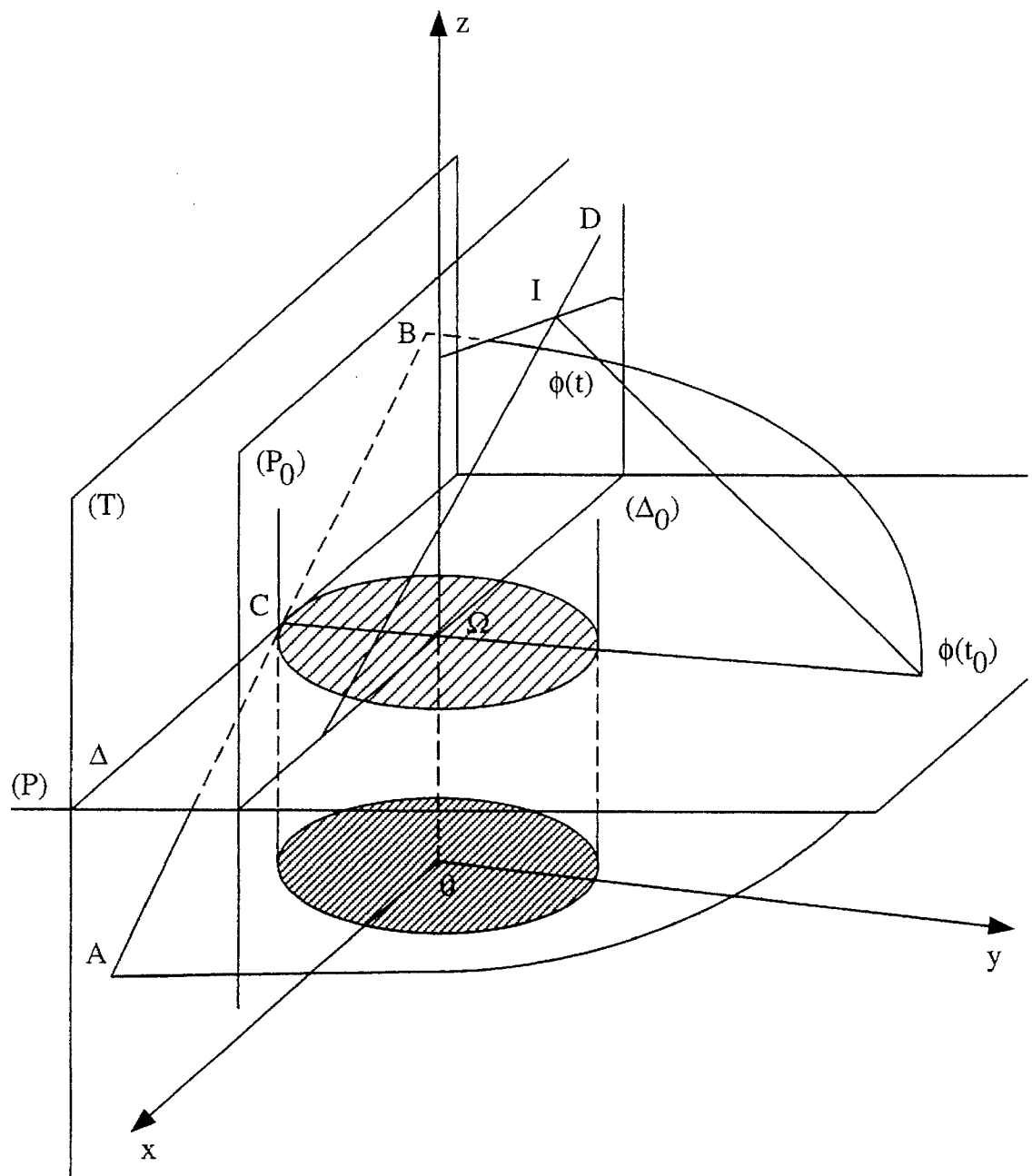
FIG. 2 illustrates a local coordinate plane ($P_0$) associated with vertex $\phi(t_0)$.
Figure 3:
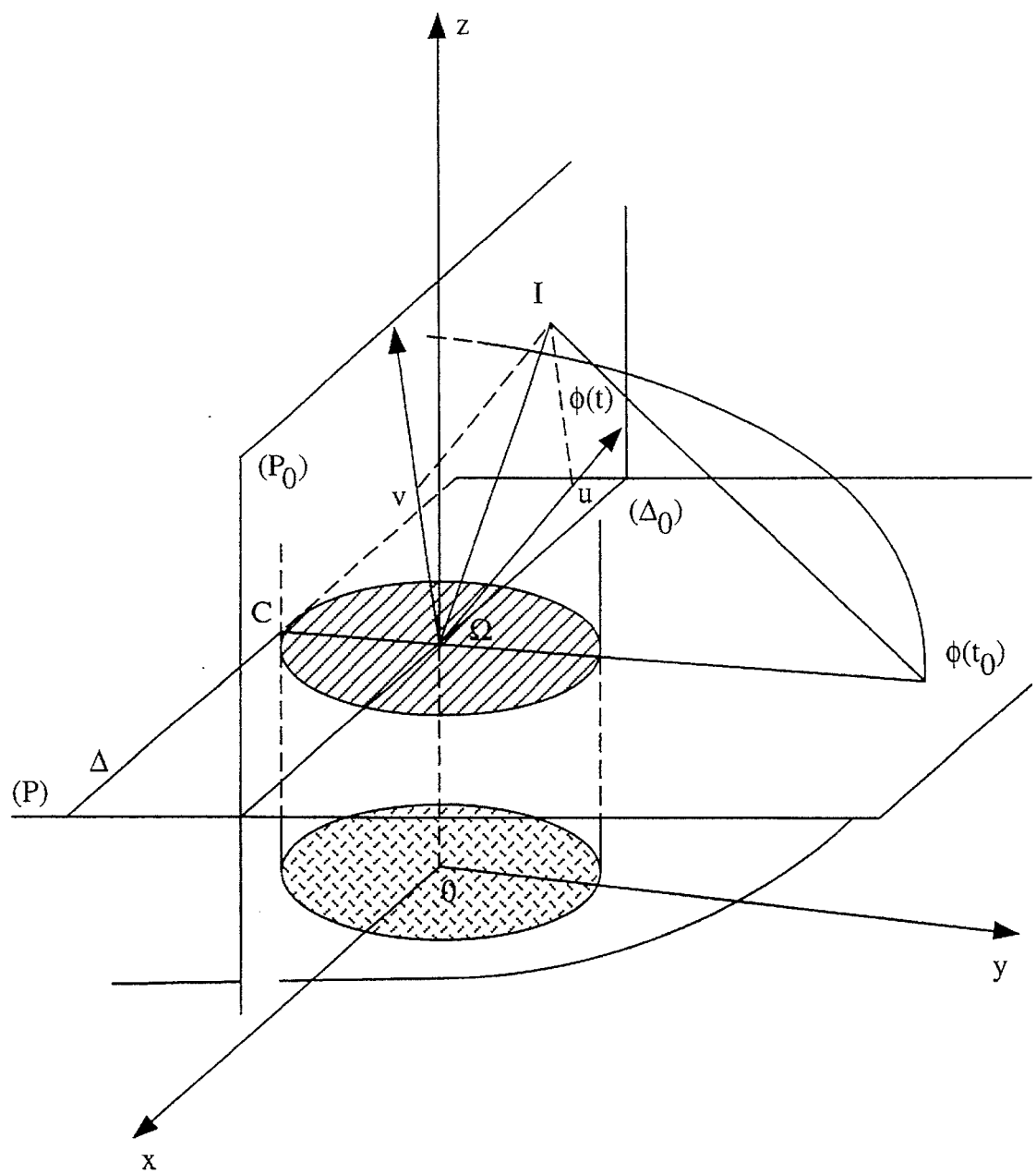
FIG. 3 further illustrates the local coordinate plane ($P_0$) associated with vertex $\phi(t_0)$ as shown in FIG. 2.

With continuing reference to FIGS. 1a–1b and further reference to FIGS. 2 and 3, the radiation detectors are all sampled concurrently to generate a current view which is stored in a current view memory or latch 40. The memory or latch 40 also stores an indication of the origin of the cone, i.e., the location of the x-ray tube and/or the location of the detector assembly. In a CT scanner in which the cone is rotating rapidly, the detectors are sampled at very short time intervals. In a nuclear camera, the output of the detectors is commonly integrated over a dwell duration at each angular position. The data from the current view memory 40 is conveyed to a partial cone-beam data memory 42 which stores a source cone or fan of data $h_t(u,v)$. More specifically, the partial cone beam data $h_t$ represents the line integrals or projections onto the plane $P_0$ along the rays $\phi$ from the origin or x-ray source. A weighting processor 44 weights each partial cone data value $h_t(u,v)$ to generate a weighted or data view $H_t(u,v)$. In a preferred embodiment, the weighting is cosine weighting of the form:

$$H_z(u,v) = h_z(u,v) \frac{R}{\sqrt{R^2 + u^2 + v^2}}, \tag{1}$$

where the weighting term is the cosine of the ray angle and R is the radius of the circle that defines the scan helix.

The object to be reconstructed is represented by a function f from $R^3$ to R, where E is the radius of a circle that defines the scan helix, i.e., the distance from the z-axis at the origin $\Omega$ to the origin of the cone. The trajectory of the x-ray source is described by a curve $\phi$ which is defined mathematically by a function $\phi$ from an interval $\Lambda$ of R to $R^3$. In the case of helical scanning, such a function $\phi$ is defined by three coordinate equations $\phi(t)=(A\cos \omega t, A\sin \omega t, \sigma t)$ for t a subset of $\Lambda$. For any direction represented by a unit vector $\alpha$ in $R^3$, the positive half-line originated at $\phi(t)$ can be represented parametrically by $\{\phi(t)+r\alpha|r \in [0,\infty]\}$ so that $h(\alpha, t)$ is defined by:

$$h(\alpha,t) = \int_0^\pi f(\phi(t) + r\alpha)dr, \tag{2}$$

is the integral of the function f along the semi-line starting at $\phi(t)$ in the direction $\alpha$. A partial cone-beam data at any instant $t_0$ may be represented by $h(\alpha, t)$, with $\alpha$ in the subset of $R^3$. $\phi(t)$ is the vertex of the partial cone at the particular instant $t_0$. The definition of the function h can be extended for all $\alpha$ in $R^3$ with $\|\alpha\| \neq 0$. Such an extended version of h is denoted hereinafter by g. The inner product of two vectors x,y in $R^3$ is denoted by <x,y>. The Fourier transform of the function f is given by:

$$\hat{f}(\xi) = \int_{R^3} f(x)e^{-2i\pi<x,\xi>}dx, \tag{3}$$

or in spherical coordinates:

$$\hat{f}(\xi) = \int_0^\infty \int_S \rho^2 \hat{f}(\rho\theta)e^{-2i\pi\rho<\xi,\theta>}d\theta d\rho, \tag{4}$$

where S denotes the unit sphere $R^3$.

The following equations give a relationship between the Fourier transform of a function f and that of a function g:

$$G(\xi, t)=F(\xi, <\phi(t), \xi>) \tag{5}$$

where, $$F(\xi,u) = \int_0^\infty \hat{f}(\rho\xi)e^{2i\pi\rho u}d\rho, \tag{6}$$

and $$G(\xi,t) = \int_{R^3} g(\alpha,t)e^{-2i\pi<\alpha,\xi>}d\alpha, \tag{7}$$

is the three-dimensional Fourier transform of g with respect to the first variable $\alpha$. From the definition itself of the function F, it can be concluded that:

$$F(\xi,u) - F(-\xi,-u) = \int_{-\infty}^\infty \hat{f}(\rho\xi)e^{2i\pi u}d\rho. \tag{8}$$

If $\theta$ is a unit vector in $R^3$, the slice projection theorem which produces the relationship between the Fourier transform of f and the one-dimensional Fourier transform of its planar integrals $R_\theta f$, it can be concluded that:

$$F(\theta,u) - F(-\theta,-u) = \frac{1}{2i\pi}(R_\theta f)'(u). \tag{9}$$

Consequently, the expression $F(\theta, u)-F(-\theta,-u)$ is 0 if $|u|>A$ for A, because the integrals along planes perpendicular to $\theta$ are 0 if the plane does not intersect the support of the function f. From this, it can be concluded that:

$$\rho \hat{f}(\rho\theta) = \int_{-A}^A (F(\theta,u) - F(-\theta,-u))e^{-2i\pi\rho u}du. \tag{10}$$

In condition 1, it is assumed that for any point x in the support of the function f, where f(x) is to be reconstructed from the cone-beam data, there exists a sub-interval $\Lambda_x$ of $\Lambda$ such that any plane going through the support of f intersects the subcurve $\phi_x$ of $\phi$ associated with the sub-interval $\Lambda_x$. From this condition and by making the change of variables defined by $u=<\phi(t),\theta>$, Equation (10) can be expressed as:

$$\rho \hat{f}(\rho\theta) = \tag{11}$$

$$\int_{\Lambda_x} (G(\theta,t) - G(-\theta,-t))|<\phi'(t),\theta>|M(\theta,t)e^{-2i\pi<\phi(t),\theta>}dt,$$

where the redundancy weight function $M(\theta,t)$ satisfies the following multiplicity condition which pertains to the number of times that the plane going through $\phi(t)$ and perpendicular to $\theta$ cuts the curve $\phi_x$:

$$\int_{\Lambda_x} |<\phi'(s),\theta>|M(\theta,s)\delta(<\phi(t) - \phi(s),\theta>)ds = 1. \tag{12}$$

If the plane perpendicular to a direction $\theta$ and going through $\phi(t)$ intersects the sub-curve $\phi_x$ at $\phi(s_0), \ldots, \phi(s_{r\theta})$, then the condition of Equation (12) can simply be expressed as:

$$M(\theta, s_0)+M(\theta, s_1)+ \ldots +M(\theta, s_{r\theta})=1 \tag{13}.$$

The term f(x) can be computed from its Fourier transform using the spherical coordinate system as follows:

$$f(x) = \int_0^\infty \rho \int_s \rho \hat{f}(\rho\theta)e^{2i\pi\rho<x,\theta>}d\theta d\rho. \tag{14}$$

Substituting Equation (11) into Equation (14), one obtains:

$$f(x) = \tag{15}$$

$$\int_0^\infty \rho \int_s \int_{\Lambda_x} (G(\theta,t) - G(-\theta,t))|<\phi'(t),$$

$$\theta>|M(\theta,t)e^{2i\pi\rho<x-\phi(t),\theta>}dt d\theta d\rho.$$

After interchanging the order of integration, one obtains:

$$f(x) = \tag{16}$$

$$\int_{\Lambda_x} \int_0^\infty \rho \int_s (G(\theta,t) - G(-\theta,t))|<\phi'(t),$$

$$\theta>|M(\theta,t)e^{2i\pi\rho<x-\phi(t),\theta>}d\theta d\rho dt.$$

Observing that $M(-\theta,t)=M(\theta,t)$, after the integration with respect to $\rho$, one has:

$$f(x) = \quad (17)$$

$$\frac{1}{2i\pi} \int_{\Lambda_x} \int_s (G(\theta,t) - G(-\theta,t)) <\phi'(t),$$

$$\theta> |M(\theta,t)\delta'(<x - \phi(t),\theta>)d\theta dt.$$

Consequently, the computation of $f(x)$ requires:

$$\Lambda_x = \{t \in \Lambda | <x-\phi(t),\theta> = 0\} \quad (18),$$

that is, the set of t is such that $\phi(t)$ is the intersection of the plane going through f and perpendicular to the direction $\theta$. The expression $f(x)$ can also be written:

$$f(x) = \quad (19)$$

$$\int_{\Lambda_x} \int_0^\infty \int_s \rho^2 \frac{(G(\theta,t) - G(-\theta,t))}{\rho^2} <\phi'(t),$$

$$\rho\theta> |M(\theta,t)e^{2i\pi<x-\phi(t),\rho\theta>}d\theta d\rho dt.$$

Observe that g and G are both homogeneous functions with respect to their first variable, and that $G(\rho\phi,t) = G(\phi,t)/\rho^2$, Equation (19) can be written as:

$$f(x) = \quad (20)$$

$$\int_{\Lambda_x} \int_0^\infty \rho^2 \int_s (G(\rho\theta,t) - G(-\rho\theta,t)) <\phi'(t),$$

$$\rho\theta> |M(\theta,t)e^{2i\pi<x-\phi(t),\rho\theta>}d\theta d\rho dt.$$

The inner double integrals of the right hand side of Equation (20) is only the three-dimensional inverse Fourier transform of the product of two functions, namely:

$$G(\xi,t) - G(-\xi,t), \text{ and } <\phi'(t), \xi> |M(\xi/\|\xi\|, t).$$

Consequently, the integrals are the three-dimensional convolution of their inverse Fourier transform. More precisely:

$$f(x) = \int_{\Lambda_x} ((g(\alpha,t) - g(-\alpha,t))^* q(\alpha,t))(x - \phi(t))dt, \quad (21)$$

with $$q(\alpha,t) = \int_{R^3} <\phi'(t), \xi> |M\left(\frac{\xi}{\|\xi\|}, t\right) e^{2i\pi<\alpha,\xi>}d\xi. \quad (22)$$

The above convolution backprojection is complex due to the redundancy of the weighting function M and is not appropriate for partial cone-beam data.

For the weighting function M constant, and with such constant set equal to 1 for simplicity, the kernel of the convolution is given by:

$$q(\alpha,t) = \int_{R^3} <\phi'(t), \xi> | e^{2i\pi<\alpha,\xi>}d\xi. \quad (23)$$

The expression $\alpha$ and $\xi$ in the coordinate system (T,U,V) with the T axis going through $\phi(t)$, and the U axis parallel to the vector $\phi'(t)$:

$$q(T,U,V,t) = \quad (24)$$

-continued $$\|\phi'(t)\| \int_{-\infty}^\infty \int_{-\infty}^\infty \int_{-\infty}^\infty |\mu| e^{2i\pi(\tau T + \mu U + \nu V)}d\tau d\mu d\nu.$$

Hence, $$q(T,U,V,t) = -\frac{\|\phi'(t)\|}{2\pi^2 U^2} \delta_T \delta_V, \quad (25)$$

i.e., q is the product of the classical ramp filter for the two-dimensional reconstruction with the delta function with respect to the variable (T,V) weighted with $\|\phi'(t)\|$. Consequently, the expression $Q(x,t) = (g(\alpha,t)^* q(\alpha,t))(x-\phi(t))$ becomes:

$$Q(x,t) = -\frac{\|\phi'(t)\|}{2\pi^2} \int_{-\infty}^\infty g(x-(0,U,0)-\phi(t),t)\frac{1}{U^2} dU. \quad (26)$$

Note that the function g is homogeneous with respect to its first variable. The convolution expression is a one-dimensional convolution of weighted line integrals or projection data along the direction of the tangent $\phi'(t)$ of the trajectory $\phi$. The kernel of the convolution is the classical ramp kernel which is used in two-dimensional slice reconstruction. Furthermore, the convolution of $g(-\alpha,t)$ is null since the object is of compact support. Thus, if M is constant, i.e., every plane goes through the point x at which $f(x)$ is to be reconstructed cuts a sub-curve $\phi_x$ at the same number of points, then the convolution is a one-dimensional convolution in the direction of $\phi'(t)$. Consequently, data can be collected in a partial cone-beam, as long as the data are not truncated in the direction of $\phi'(t)$, for any instance t in $\Lambda_x$.

Although the exact reconstruction formula requires a non-constant weighting function $M(\theta,t)$ which satisfies the redundancy condition stated above, based on the simplicity of the convolution expression, the weighting function M can be written as the sum of a constant C and a non-constant function N, i.e.:

$$M(\theta,t) = C + N(\theta, t) \quad (27).$$

With this decomposition, the convolved data is the sum of two terms. The first term corresponds to C; and the second term corresponds to the weighting function N. Because the first term requires a one-dimensional convolution in the direction $\phi'(t)$, it can be assumed that the partial cone-beam data is collected within a rectangle with one side parallel to $\phi'(t)$.

In condition 2, it is assumed that at any instant t, the data of the partial cone beam is not truncated in the direction $\phi'(t)$ and there exists a positive integer K. The integer K has the property that if at time t, the data is truncated along a direction $\Delta$, then the plane defined by the line $\Delta$ and the vertex $\phi(t)$ either (i) intersects $\phi_x$ exactly K times or (ii) intersects $\phi_x$ at another vertex $\phi(t')$ for which the data along the line $\Delta'$ orthogonal to the plane is not truncated.

Furthermore, it is assumed that along that side, the data is not truncated. The redundancy condition on the function M requires N to satisfy the following condition:

$$\int_{\Lambda_x} N(\theta, s) <\phi'(s), \theta> |\delta(<\phi(t) - \phi(s), \theta>)ds = \quad (28)$$

-continued $$1 - C \int_{\Lambda_x} |<\phi'(s), \theta>|\delta(<\phi(t) - \phi(s), \theta>)ds.$$

Observe that if $W(\theta,t) \geq 0$ and satisfies the condition:

$$\int_{\Lambda_x} W(\theta, s)|<\phi'(s), \theta>|\delta(<\phi(t) - \phi(s), \theta>) \neq 0, \quad (29)$$

then the function N can be defined by:

$$N(\theta, t) = \frac{\left(1 - C \int_{\Lambda_x} |<\phi'(s), \theta>|\delta(<\phi(t) - \phi(s), \theta>)ds\right) \times W(\theta, t)}{\int_{\Lambda_x} W(\theta, s)|<\phi'(s), \theta>|\delta(<\phi(t) - \phi(s), \theta>)ds}. \quad (30)$$

W is chosen such that the computation of the convolved data does not use the truncated data. Using the truncated data would allow $N(\theta,t)=0$.

Thus, to simplify the reconstruction, the reconstruction formula is chosen to be:

$$f(x) = \int_{\Lambda_x} (Q_1(x, t) + Q_2(x, t))dt, \quad (31)$$

where $Q_1$ is the convolved data corresponding to C which is the one-dimensional convolution of the weighted data with the classical ramp function in the direction $\phi'(t)$ and the second term $Q_2$ is given by:

$$Q_2(x, t) = \int_0^\infty \rho \int_s (G(\theta, t) - \quad (32)$$

$$G(-\theta, t))|<\phi'(t), \theta>|N(\theta, t) \, e^{2i\pi\rho<x-\phi(t),\theta>} \, d\theta d\rho,$$

Thus, it follows that:

$$G(\theta, t) - G(-\theta, t) = -\frac{i}{2\pi} \int_s g(\alpha, t)\delta'(<\alpha, \theta>)d\alpha. \quad (33)$$

The right hand side of Equation (33) is only the product of $-i/2\pi$, with the integral of the directional derivative of propagation data along a line in the detector plane and orthogonal to the direction $\theta$. Consequently, the computation of $Q_2$ does not require the data along that line with the truncated data. To insure that such choice is always possible, W is selected accordingly. For this reason, appropriate conditions are set on the curve $\phi$ traversed by the x-ray source or origin of the cone-beam relative to the axis z. A spiral or a partial spiral extending from A to B satisfies the conditions.

The weighting processor 44 performs the constant weighting component weighting of the data while a second factor processor 46 calculates the non-constant weighting factor. The weighted data from the processor 44 is conveyed to a first or $Q_1$ processor 48 which calculates the $Q_1$ component and to a second or $Q_2$ processor 50 which calculates the $Q_2$ component with the non-constant weighting function from the weighting function processor 46. A processor 52 computes the sum of $Q_1$ and $Q_2$ and the sum is backprojected by a three-dimensional backprojector 54, generally as described by Equations (19)–(21) and as described in greater detail below.

Figure 4:
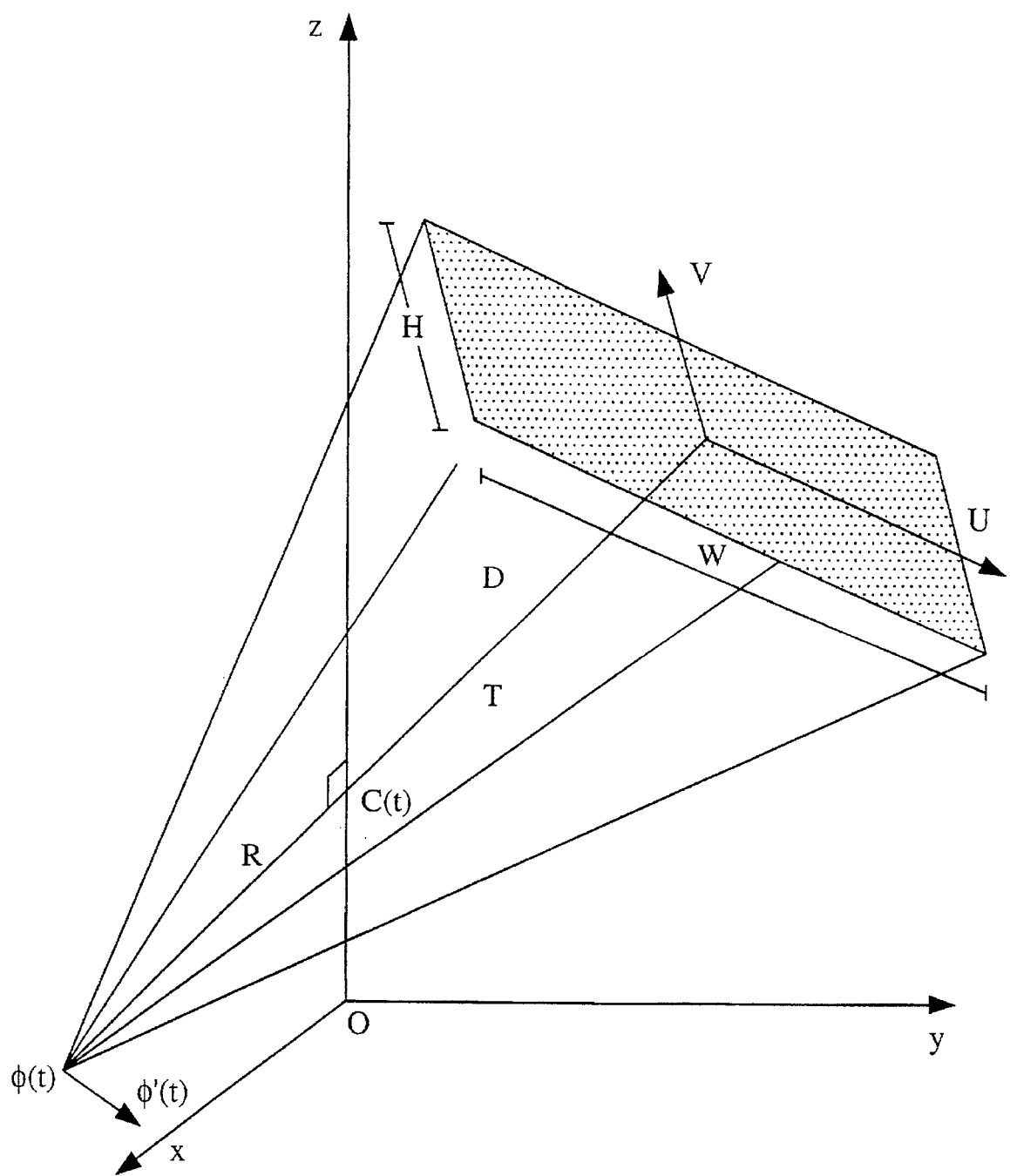
FIG. 4 illustrates a partial cone-beam data at any instance t.
Figure 5:
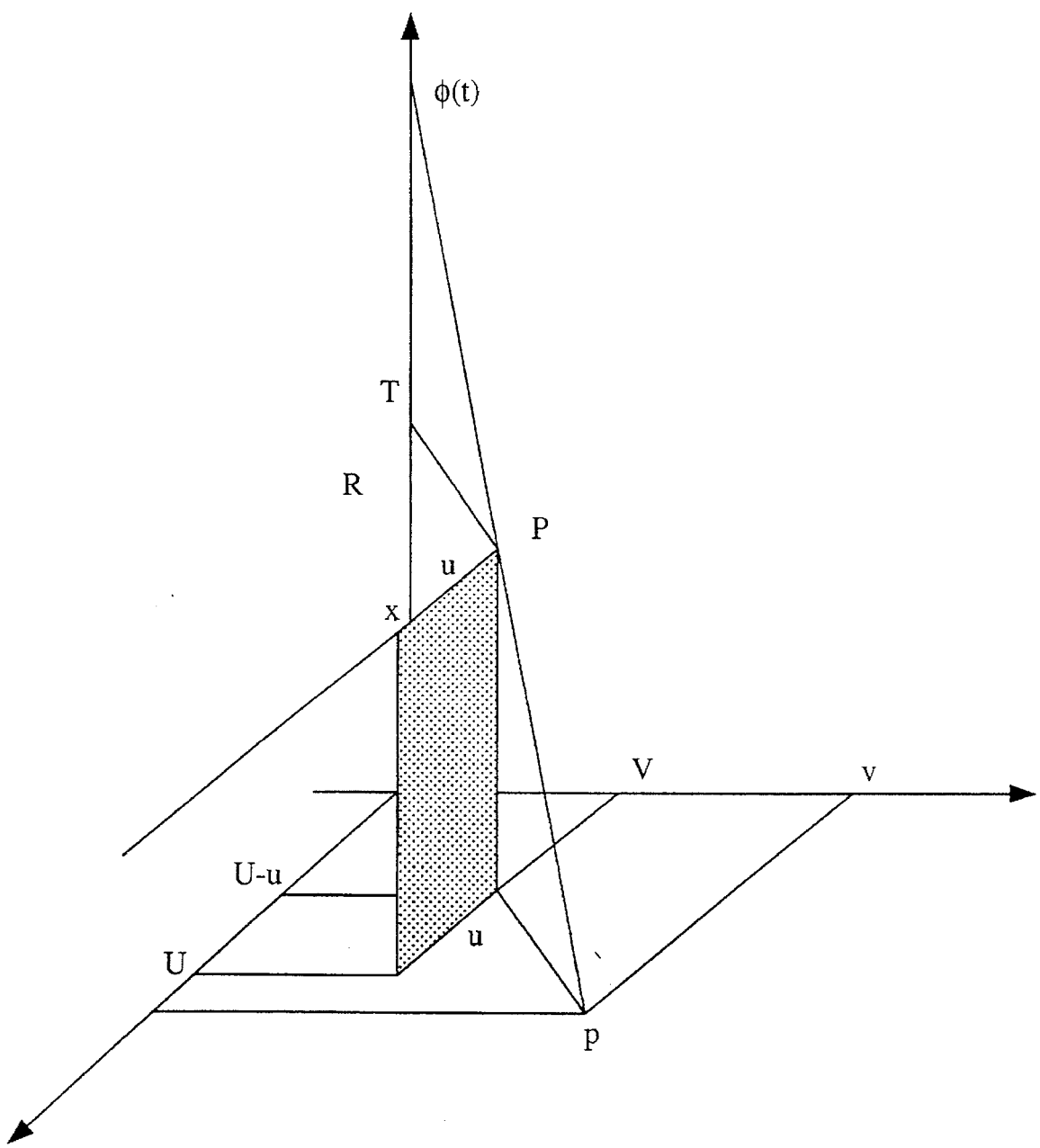
FIG. 5 illustrates a function $h_t(u,v)$ as an integral of a function f along the line from $\phi(t)$ to a point $(u,v)$ in a plane defined by $C(t)$ of the U and V axes.
Figure 6:
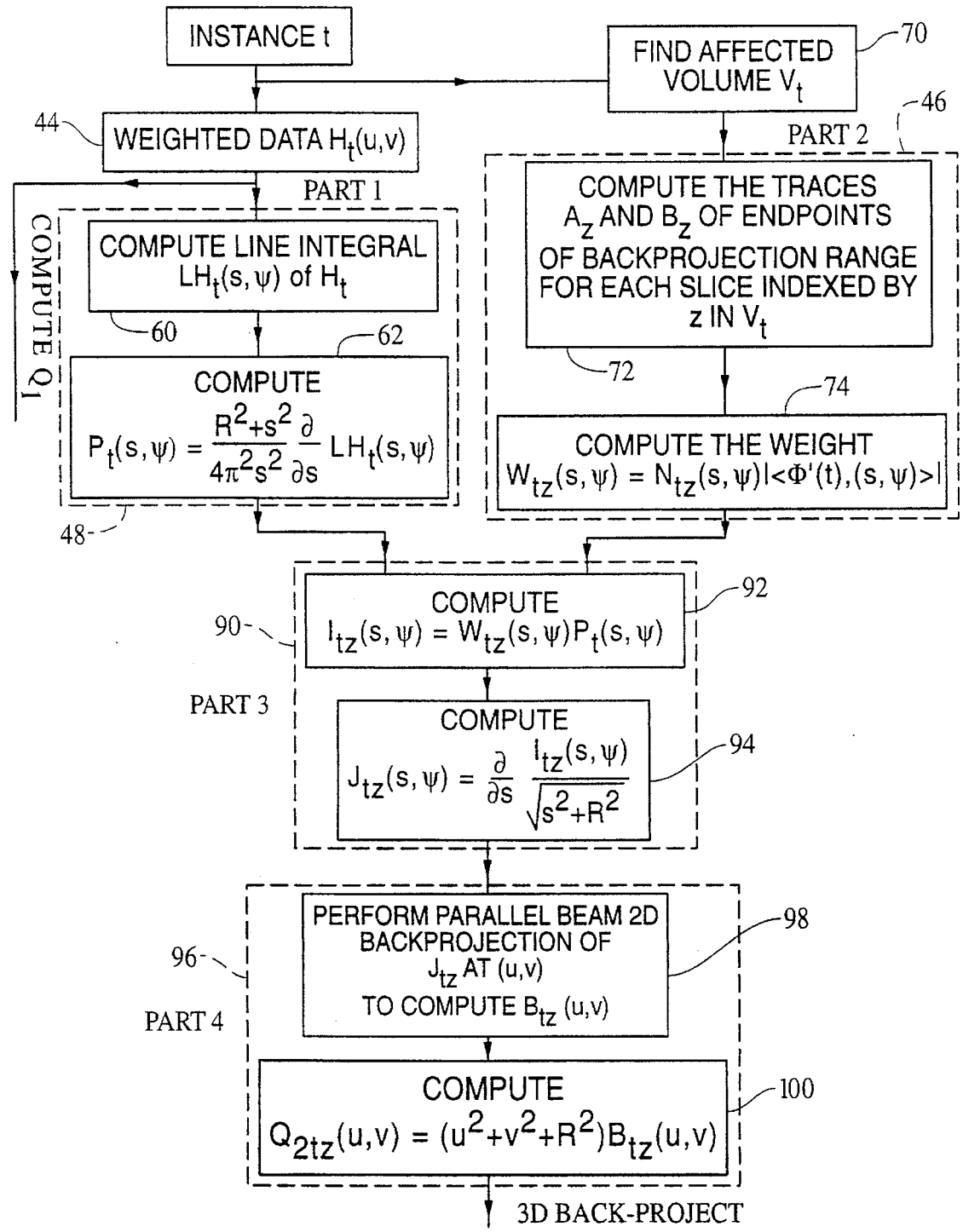
FIG. 6 illustrates a block diagram of a reconstruction algorithm for determining $Q_2$.

With reference to FIGS. 4, 5, and 6, we start first in the (T,U,V) coordinate system. In this coordinate system $Q_1$ is evaluated as:

$$Q_1(x, t) = -\frac{\|\phi'(t)\|}{2\pi^2} \int_{-\infty}^{\infty} g(x - (0, u, 0) - \phi(t), t) \frac{1}{u^2} \, du, \quad (34)$$

To simplify the coordinate transformation, the center of the coordinate system (T,U,V) is chosen to be the orthogonal projection C(t) of $\phi(t)$ onto the z-axis. This coordinate system is simply the translation of the coordinate system of FIG. 5, with the translation vector $D_{96}$, where $\tau$ is the unit vector along the T-axis. In this new coordinate system, the coordinates (T,U,V) of the reconstruction point x can be obtained from its original coordinates (X,Y,Z) by multiplying the column matrix (X,Y, Z−σt)$^t$ with the 3×3 rotation matrix A(t) which consists of the coordinates of the unit vectors τ,μ,ν along the T,U, and V-axes respectively. For $\phi(t)=(R\cos\omega t, R\sin\omega t, \sigma t)$:

$$\tau = [\cos\omega t \sin\omega t \; 0] \quad (35a),$$

$$\mu = [-R\omega\sin\omega t \; R\omega\cos\omega t \; \sigma]/(R^2\omega^2+\sigma^2)^{1/2} \text{ and} \quad (35b),$$

$$\nu = [\sigma\sin\omega t - \sigma\cos\omega t \; R\omega]/(R^2\omega^2+\sigma^2)^{1/2}. \quad (35c).$$

It remains then to evaluate the integral expression of $Q_1$ using a sample from the set of line integrals $h_t$ which are estimated from the partial cone-beam projection data. Conforming to the choice of the new local coordinate system, $h_t(u,v)$ is defined as the integral of the function f along the line from $\phi(t)$ to the point (u,v) in the plane defined by C(t), the U and V-axes of the local coordinate system. For P as the point x−(0,u,0) as shown in FIG. 3, by the homogeneity property of g, one can express g from the corresponding line integrals as follows:

$$g(x - (0, u, 0) - \phi(t), t) = \quad (36)$$

$$\frac{1}{\|P - \phi(t)\|} \, g\left(\frac{P - \phi(t)}{\|P - \phi(t)\|}, t\right).$$

For p as the intersection of the line from $\phi(t)$ to P with the (C(t),U,V) plane, the coordinates of the point p in the coordinate system are (0,w(U−u),wV) with w=R/(R−T). Because $p=\phi(t)+w(P-\phi(t))=(R,0,0)+w(T-R,U-u,V)$, and because w is the constant which makes the first coordinate of p null, then:

$$p - \phi(t) = w(P - \phi(t)) \quad (37a).$$

Hence, $$\frac{1}{\|p - \phi(t)\|} = \frac{w}{\|P - \phi(t)\|}, \quad (37b)$$

or:

$$\frac{1}{\|p - \phi(t)\|} = \frac{w}{\sqrt{R^2 + w^2(U - u)^2 + w^2V^2}}. \quad (37c)$$

Substituting into Equation (36):

$$g(X - (0, u, 0) - \phi(t), t) = \quad (38)$$

$$\frac{w}{\sqrt{R^2 + w^2(U - u)^2 + w^2V^2}} \, h_t(w(U - u), wV).$$

Accordingly, the expression of $Q_1$ becomes:

$$Q_1(x, t) = -w \frac{\|\phi'(t)\|}{2\pi^2} \int_{-\infty}^{\infty} \frac{h_r(w(U-u), wV)}{\sqrt{R^2 + w^2(U-u)^2 + w^2V^2}} \frac{1}{u^2} du. \quad (39)$$

When v is defined as equal to wV, and after a change of the variable of integration is made, $Q_1$ becomes:

$$Q_1(x, t) = -w^2 \int_{-\infty}^{\infty} H_r(u, v) \frac{1}{(wU-u)^2} du, \quad (40)$$

where $H_r(u,v)$ is defined by Equation (1), where $R=\|\phi'(t)\|/2\pi^2$. In other words $Q_1$ (x,t) is obtained by convolving $H_r(u,v)$ with the classical ramp kernel with respect to the first variable u and evaluating it at wU, where U is the second coordinate of x in the local coordinate system. $H_r(u,v)$ is the projection data $h_r(u,v)$ weighted with the constant divided by the distance from $\phi(t)$ to the point (u,v) on the plane (C(t),U,V).

Thus, the term $Q_1$ is essentially a one-dimensional convolution of the weighted data with the classical ramp 2D reconstruction filter. By contrast, the computation of $Q_2$ involves the computation of a weighting function N based on a knowledge of the number of intersection points of a plane with a portion of the helix $\phi$, the trajectory of the vertex of the cones. Accordingly, before calculating $Q_2$, one first establishes the number of intersection points.

With reference again to FIGS. 1 and 2, and further reference to FIG. 6, the equation for the local coordinate planes ($\cos\omega t_0$, $\sin\omega t_0$, 0) is:

$$x\cos\omega t_0 + y\sin\omega t_0 = 0 \quad (41).$$

A plane (Q) containing $\phi(t_0)$ and a point x of the support of the object intersects $\phi$ at another point $\phi(t)$ if and only if the intersection I of the line joining the two vertices $\phi(t)$ and $\phi(t_0)$ with the coordinate plane ($P_0$) associated with $\phi(t_0)$ belongs to the intersection line D of the plane (Q) with the plane ($P_0$). Note that I belongs to both planes (Q) and ($P_0$). Conversely, when the intersection line D of (Q) with ($P_0$) contains the point I which is the intersection of $\phi(t_0),\phi(t)$ with the plane ($P_0$), then $\phi(t)$ belongs to (Q), i.e., (Q) intersects $\phi$ at $\phi(t)$. To count the number of intersection points of the plane (Q) besides $\phi(t_0)$, the number of intersections points of the line D with the trace of the helix on ($P_0$) is counted.

The trace of $\phi$ on the local coordinate plane ($P_0$) associated with $\phi(t_0)$ is the set of intersection points I of the line $\phi(t_0)\phi(t)$ with the plane ($P_0$) as t varies in an interval containing $t_0$. Similarly, the trace of a point x onto the local coordinate plane ($P_0$) is defined by the point of the intersection M at the line $\phi(t_0),x$ with the plane ($P_0$).

The trace of $\phi$ contains two branches of curves which intersect the u-axis at infinity, because the line $\phi(t_0)\phi(t)$ becomes tangent to $\phi$ as t tends to $t_0$. The coordinates of the intersection point I can be written as a point of the line $\phi(t_0)\phi(t)$ as:

$I=(R\cos\omega t_0+rR(\cos\omega t-\cos\omega t_0),$ $R\sin\omega t_0+rR(\sin\omega t-\sin\omega t_0),$ (42), $\sigma t_0+r\sigma(t-t_0))$ where r is a real number. Because the point I belongs to the local coordinate plane, the coordinates of I must satisfy the above equation of the local coordinate plane. Accordingly, $r=(1-\cos\omega(t-t_0))^{-1}$. The Equation (42) coordinates of I are with respect to the original coordinate system Oxyz.

With reference to FIG. 3, to obtain the coordinates (u,v) of I with respect to the local coordinate system, it suffices to compute the inner product of the vector $\Omega I$ with the unit vectors:

$\mu = [-R\omega\sin\omega t_0, R\omega\cos\omega t_0, \sigma]/(R^2\omega^2+\sigma^2)^{1/2}$ and (43a), $\nu = [\sigma\sin\omega t_0, -\sigma\cos\omega t_0, R\omega]/(R^2\omega^2+\sigma^2)^{1/2}$ (43b).

More specifically, $u = \langle \Omega I, \mu \rangle$ and $v = \langle \Omega I, \nu \rangle$. Because:

$\Omega I = (R\cos\omega t_0 + rR(\cos\omega t - \cos\omega t_0),$ $R\sin\omega t_0 + rR(\sin\omega t - \sin\omega t_0),$ (44), $r\sigma(t-t_0))$ it follows that:

$$u = r \frac{R^2\omega\sin\omega(t-t_0) + \sigma^2(t-t_0)}{\sqrt{R^2w^2 + \sigma^2}}, \quad (45a)$$

and, $$v = R\sigma r \frac{\sin\omega(t_0-t) + \omega(t-t_0)}{\sqrt{R^2\omega^2 + \sigma^2}}, \quad (45b)$$

as $t \to t_0$, $u \to \pm\infty$, and $v \to 0$, for $t=t_0\pm\pi/\omega$, Equations (45a) and (45b) become:

$$u = \pm \frac{\sigma^2\pi}{2\omega\sqrt{R^2\omega^2 + \sigma^2}}, \quad (46a)$$

$$v = \pm \frac{R\sigma\pi}{2\sqrt{R^2\omega^2 + \sigma^2}}. \quad (46b)$$

The derivatives of u and v with respect to t are:

$$\frac{du}{dt} = \frac{(\sigma^2 - R^2\omega^2)(1 - \cos\omega(t-t_0)) - \sigma^2\omega(t-t_0)\sin\omega(t-t_0)}{\sqrt{R^2\omega^2 + \sigma^2}(1 - \cos\omega(t-t_0))^2}, \quad (47a)$$

$$\frac{dv}{dt} = \frac{R\sigma\omega}{\sqrt{R^2\omega^2 + \sigma^2}} \frac{(2(1 - \cos\omega(t-t_0)) - \omega(t-t_0)\sin\omega(t-t_0))}{(1 - \cos\omega(t-t_0))^2}. \quad (47b)$$

Figure 7:
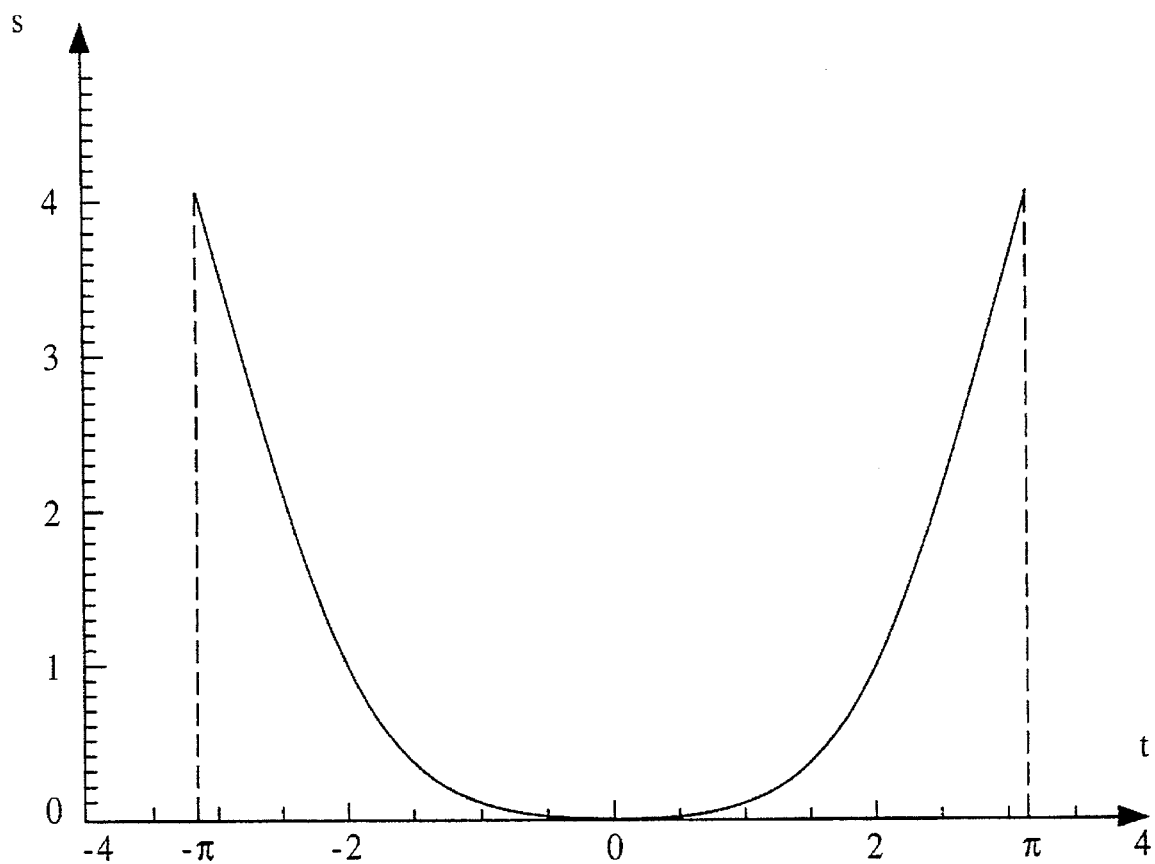
FIG. 7 illustrates a graph of s(t)=2(1-cost)-tsint.
Figure 8:
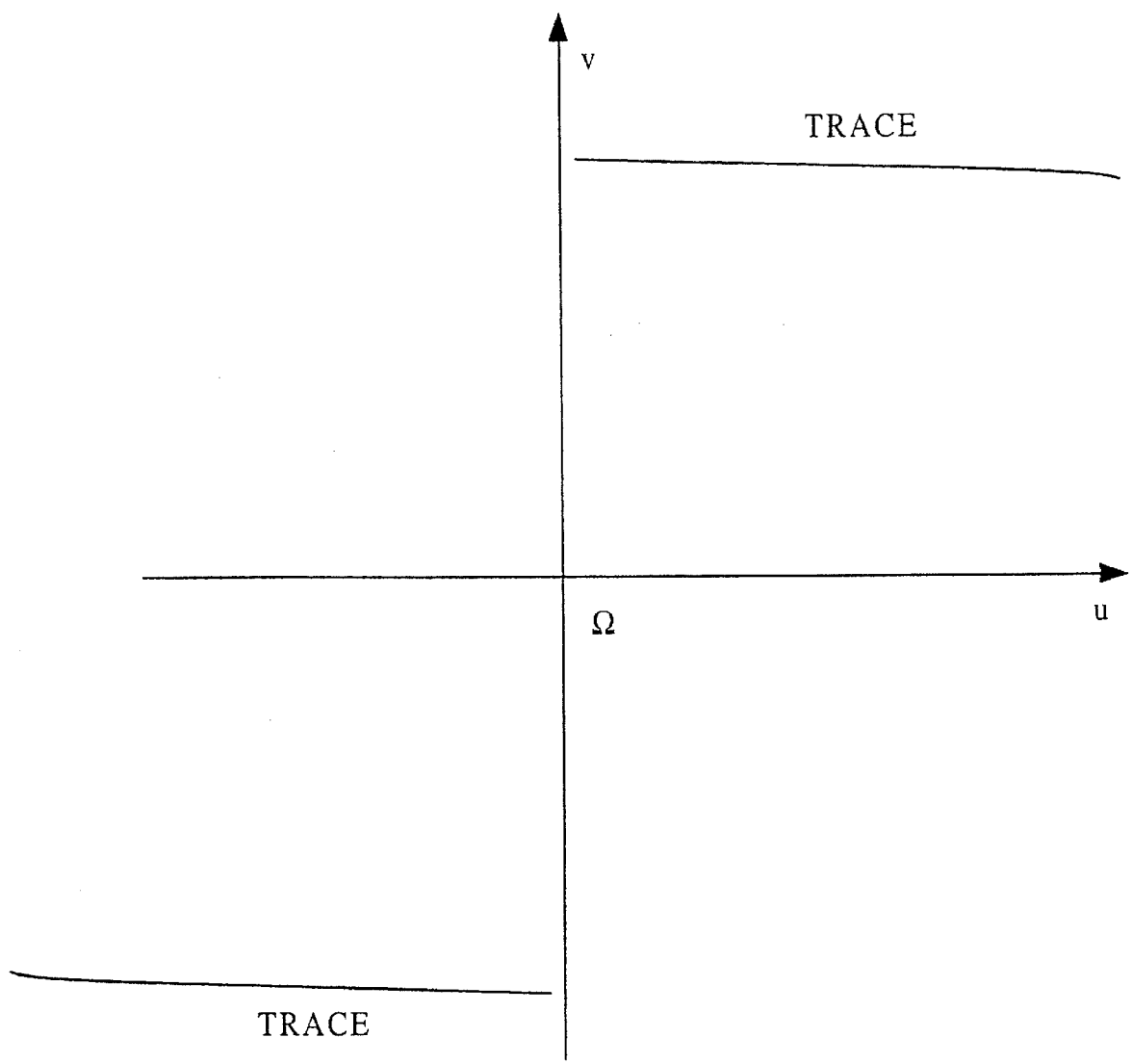
FIG. 8 illustrates the trace of the helix on a local coordinate plane in (u,v) space.
Figure 9:
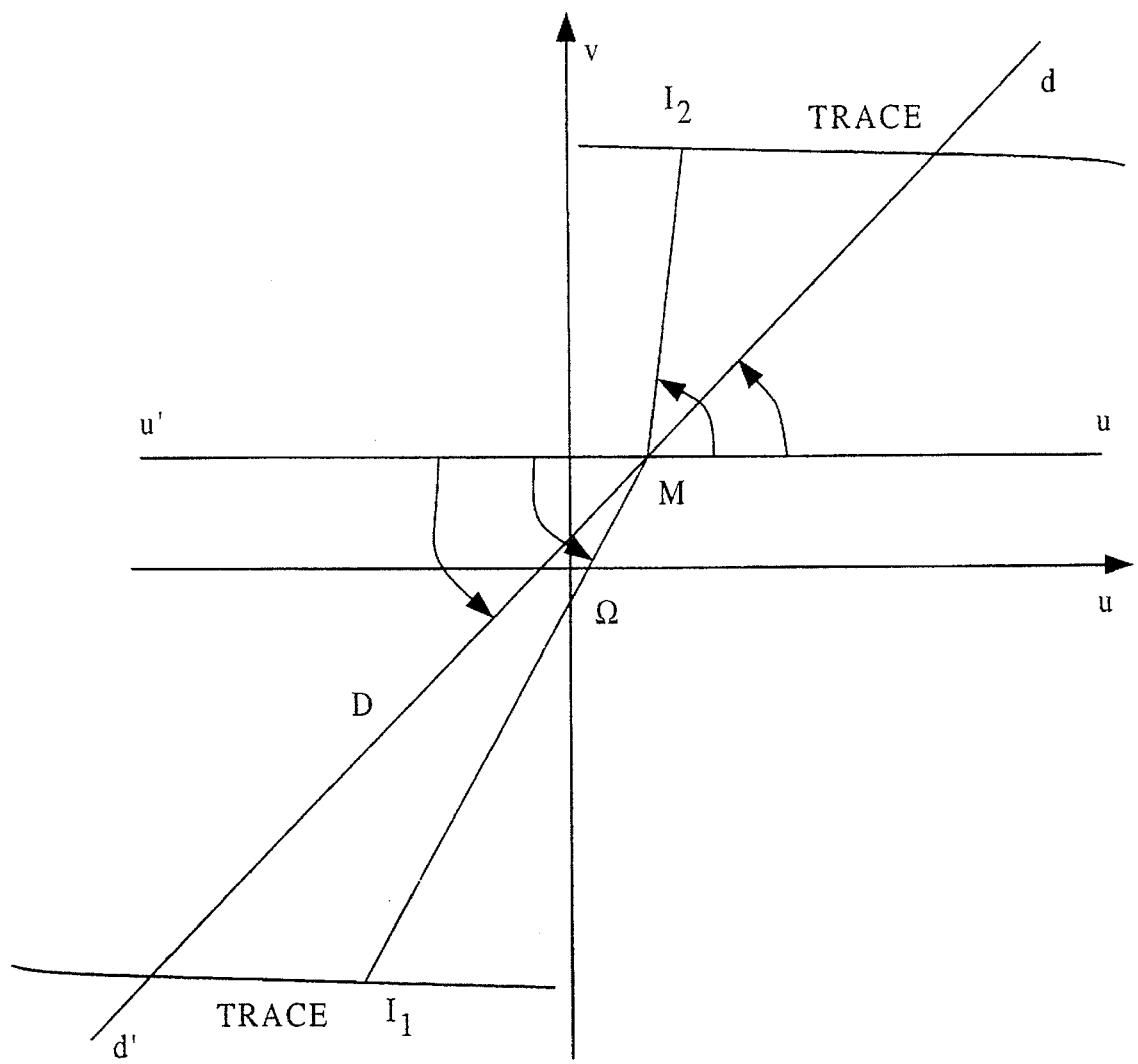
FIG. 9 illustrates M as the trace of x on ($P_0$) and D as the intersection of (Q) with ($P_0$)

For $\omega$ and $\sigma > 0$, the derivative of u with respect to t is negative, and that the derivative of v is positive. Note FIG. 7. This analysis of u and v shows that the trace of the helix on a local coordinate plane has a graph in the (u,v) space as illustrated in FIG. 8. This analysis suggests the following practical criteria to count the number of intersection points of a plane going through a point of reconstruction with part of a helix. With reference to FIG. 9, $[t_1, t_2]$ is an interval containing $t_0$ and $I_1$, $I_2$ is the trace of $\phi(t_1)$ and $\phi(t_2)$ on the local coordinate planes ($P_0$) associated to $t_0$, respectively. (Q) is a plane containing $\phi(t_0)$ and a point x on the support of the object. M is the trace of x on ($P_0$) and D is the intersection of (Q) with ($P_0$).

Looking to the first criteria, (Q) intersects $\phi$ at $\phi(t)$ with t in $[t_1, t_2]$ if and only if D intersects the portion of the branch of the trace of the helix from $-\infty$ to $I_1$. Practically, this is equivalent to the angle between the half lines Mu' and Md' being less than the angle between Mu' and $MI_1$.

Looking to the second criteria, (Q) intersects $\phi$ at $\phi(t)$ with t in $[t_0, t_2]$ if and only if D intersects the portion of the branch of the trace of the helix from $I_2$ to $\infty$. Practically, this is equivalent to the angle between the half lines Mu and Md being less than the angle between Mu and $MI_2$.

$Q_2$ as defined in Equations (32) and (33) can be further quantified by splitting the unit sphere into the union of two disjoint sphere halves, namely S/2 and −S/2, the upper and lower half unit spheres. Equation (32) then reduces to:

$$Q_2(x, t) = \int_0^\infty \int_{S/2} P(\theta, t)\rho e^{2i\pi\rho<x-\phi(t),\theta>} d\theta d\rho + \quad (48)$$

$$\int_0^\infty \int_{-S/2} P(\theta, t)\rho e^{2i\pi\rho<x-\phi(t),\theta>} d\theta d\rho,$$

where:

$$P(\theta,t) = (G(\theta, t) - G(-\theta, t))I<\phi'(t),\theta>IN(\theta,t) \quad (49).$$

Substituting $-\theta$ for $\theta$ in the second integral of $Q_2$ and because $I(-\theta, t) = -I(\theta, t)$, Equation (48) becomes:

$$Q_2(x, t) = \int_0^\infty \int_{S/2} P(\theta, t)\rho e^{2i\pi\rho<x-\phi(t),\theta>} d\theta d\rho - \quad (50a)$$

$$\int_0^\infty \int_{S/2} P(\theta, t)\rho e^{2i\pi\rho<x-\phi(t),\theta>} d\theta d\rho.$$

Hence, Equation (32) becomes:

$$Q_2(x, t) = \int_{S/2} (G(\theta, t) - \quad (50b)$$

$$G(-\theta, t))I<\phi'(t), \theta>IN(\theta, t) \int_{-\infty}^\infty \rho e^{2i\pi\rho<x-\phi(t),\theta>} d\theta d\rho$$

Integrating with respect to the variable $\rho$ and replacing $G(\theta,t) - G(-\theta,t)$ by the above-expression, one obtains:

$$Q_2(x, t) = \frac{1}{4\pi^2} \int_{S/2} \int_S g(\alpha, t)\delta'(<\alpha, \theta>)d\alpha I<\phi'(t), \theta>IN(\theta, t)\delta'(<x - \phi(t), \theta>)d\theta. \quad (51)$$

Figure 10:
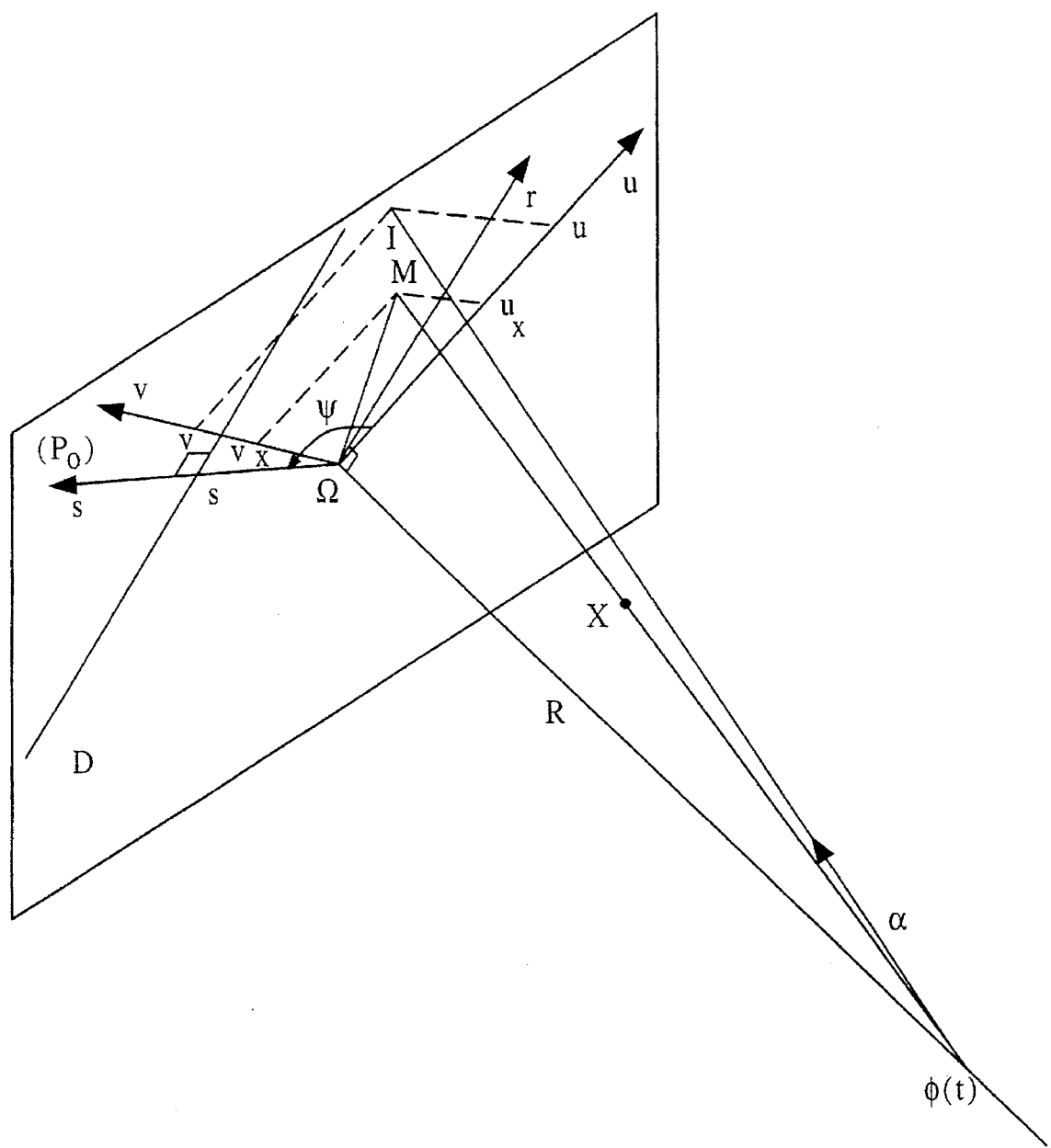
FIG. 10 is illustrates the integral of the function $H_r$ along a line defined by polar parameter $(s,\psi)$.

Equation (51) is similar to Equation (11) of the Defrise and Clack reference of record, but with a different weighting function $N(\theta, t)$. The following notation is used in transposing their results:

(u,v) is the local coordinates of the intersection of the local coordinate plane ($P_0$) with the line going through $\phi(t)$ and parallel to the direction $\alpha$;

($u_x$, $v_x$) is the local coordinates of the trace of the reconstruction point x;

(s, $\psi$) is the polar parameters of the intersection of the local coordinate plane ($P_0$) with the plane perpendicular to the direction $\theta$ and going through x, and $\phi(t)$; and, $LH_t(s,\psi)$ is the integral of the function $H_t$ along the line defined by the polar parameter (s,$\psi$), where s is the distance from $\Omega$ to the line, and $\psi$ is the angle between the u-axis and the line, see FIG. 10.

With this notation, $Q_2$ can be carried out as follows:

$$Q_2(x,t) = Q_2(u_x, v_x, t) = \quad (52)$$

-continued $$\frac{u_x^2 + v_x^2 + R^2}{4\pi^2\|x - \phi(t)\|^2} \int_0^\pi \frac{\partial}{\partial s}\left[\frac{I(s,\psi,t)}{\sqrt{s^2 + R^2}}\right]_{s=u_x\cos\psi+v_x\sin\psi} d\psi,$$

where:

$$I(s,\psi,t) = -\int_S g(\alpha,t)\delta'(<\alpha,\theta>)d\alpha I<\phi'(t),\theta>IN(\theta,t), \quad (53)$$

may be computed using Grangeat's fundamental relationship by multiplying $I<\phi'(t),\theta>IN(\theta,t)$ with the weighted partial derivatives of the line integrals of $H_t$:

$$-\int_S g(\alpha,t)\delta'(<\alpha,\theta>)d\alpha = \frac{R^2 + s^2}{R^2} \frac{\partial}{\partial s} LH_t(s,\psi), \quad (54)$$

with $H_t$ being a function defined on the local coordinate plane in a fashion similar to the one defined for computing $Q_1$, except for a constant factor:

$$H_t(u,v) = \frac{Rg(\alpha,t)}{\sqrt{R^2 + u^2 + v^2}}. \quad (55)$$

In other words, $Q_2$ is obtained by two-dimensionally backprojecting at the trace of the reconstruction point, partial derivatives of weighted partial derivatives of line integrals of weighted partial cone-beam data.

Figure 11:
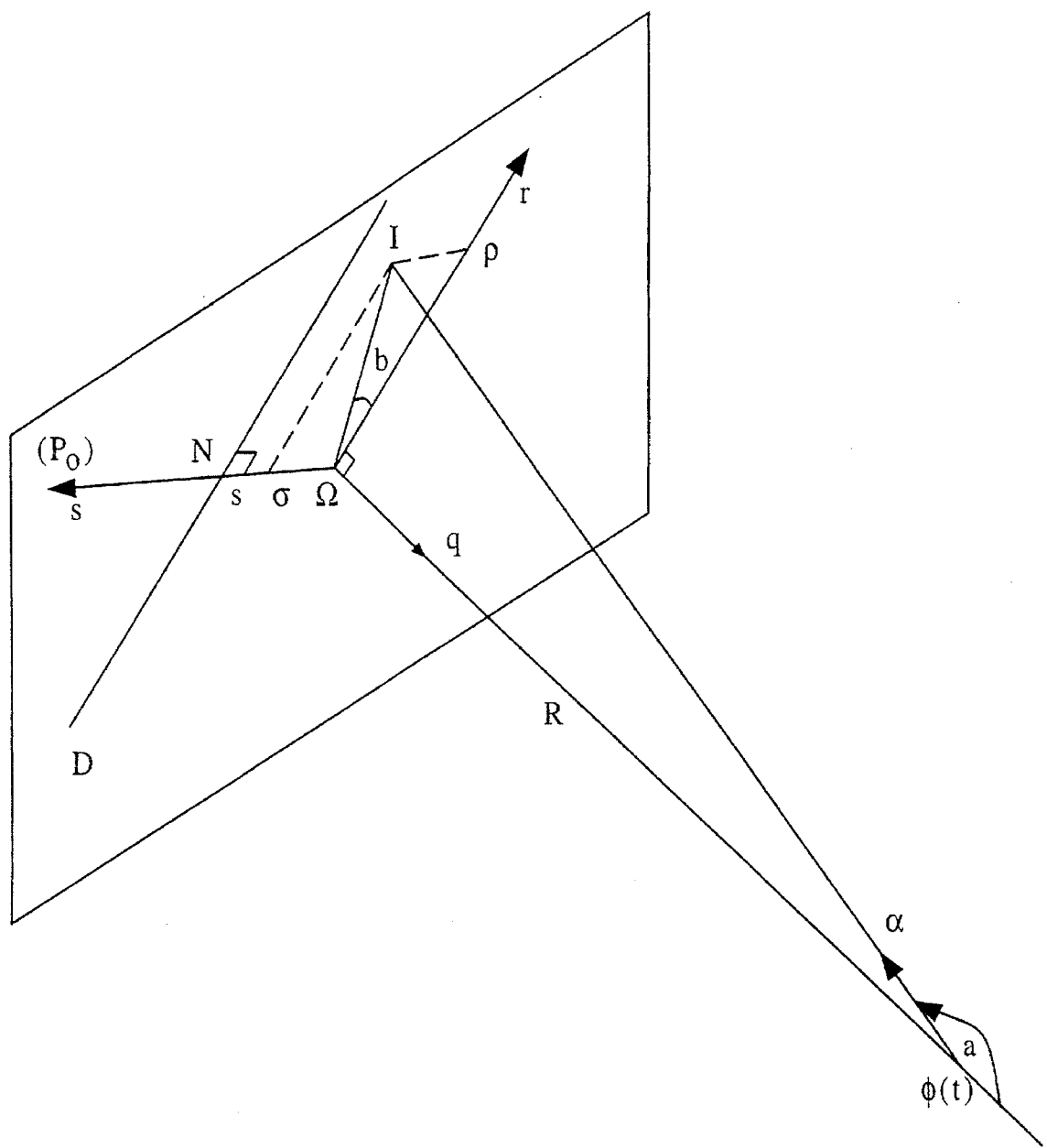
FIG. 11 illustrates a coordinate system $\omega$, q,r,s.

With reference to FIG. 11, a coordinate system $\Omega qrs$ is defined with $\Omega q$ along $\Omega\phi(t)$, $\Omega r$ parallel to the intersection line D of the color coordinate plane with the plane perpendicular to the unit vector $\theta$, and perpendicular to D. In this coordinate system, the coordinates of the vector $\alpha$ are $(\rho,\sigma,R)/(\rho^2+\sigma^2+R^2)^{1/2}$ and those of the intersection point N of the line D with the axis $\Omega s$ are (0,s,0). Because the vector $\theta$ is perpendicular to both vectors (0,s,0) and the vector $N\phi(t)$ with coordinates (0,−s,R), it follows that the coordinates of $\theta$ are proportional to the exterior product of the two vectors. Consequently, the coordinates of $\theta$ are (0,R,−s)/$(S^2+R^2)^{1/2}$, and hence:

$$<\alpha,\theta> = \frac{R(\sigma - s)}{\sqrt{\rho^2 + \sigma^2 + R^2} \sqrt{s^2 + R^2}}. \quad (56)$$

If a and b are the polar and azimuthal angles of the unit vectors $\alpha$, see FIG. 11, then:

$$d\alpha = \sin(a)dadb \quad (57).$$

Because:

$$\cos(a) = \frac{-R}{\sqrt{\rho^2 + \sigma^2 + R^2}}, \quad (58a)$$

and, $$b = \tan^{-1}\left(\frac{\sigma}{\rho}\right), \quad (58b)$$

it follows that the Jacobian is:

$$\frac{\partial(\cos(a),b)}{\partial(\rho,\sigma)} = R(\rho^2 + \sigma^2 + R^2)^{-3/2}. \quad (58c)$$

Hence, Equation (54) becomes:

$$\int_2 g(\alpha,t)\delta'(<\alpha,\theta>)d\alpha = \int_{-\infty}^{\infty}\int_{-\infty}^{\infty}(\rho^2+\sigma^2+R^2)^{-\frac{3}{2}}h_t(\rho,\sigma)\delta'\left(\frac{R(\sigma-s)}{\sqrt{\rho^2+\sigma^2+R^2}\sqrt{s^2+R^2}}\right)d\sigma d\rho, \quad (59)$$

where $h_t(\rho,\sigma)=Rg(\alpha,t)$. After integrating with respect to $\sigma$, this becomes:

$$\int_s g(\alpha,t)\delta'(<\alpha,\theta>)d\alpha = \quad (60)$$

$$-\frac{s^2+R^2}{R^2}\int_{-\infty}^{\infty}\frac{\partial}{\partial s}\frac{h_t(\rho,s)}{\sqrt{\rho^2+s^2+R^2}}d\rho.$$

From this, a constructive form of $Q_2$ can be developed. In the local coordinate system in which integration is carried out with respect to $\theta$ over $S/2$, the vector $\theta$ can be obtained by multiplying its coordinates with respect to $(r,s)$ coordinate system with the rotation matrix introduced by the angle $(\pi/2-\psi)$. Consequently:

$$\theta = \frac{1}{\sqrt{s^2+R^2}}(R\cos\psi, R\sin\psi, -s). \quad (61)$$

With respect to the local coordinate system:

$$\frac{x-\phi(t)}{\|x-\phi(t)\|} = \frac{1}{\sqrt{u_x^2+v_x^2+R^2}}(u_x,v_x,R). \quad (62)$$

Consequently:

$$<x-\phi(t),\theta> = \quad (63)$$

$$\frac{R\|x-\phi(t)\|}{\sqrt{u_x^2+v_x^2+R^2}\sqrt{s^2+R^2}}(u_x\cos\psi+v_x\sin\psi-s).$$

Moreover, if a and b are the polar and the azimuthal angles of the vector $\theta$, then:

$$\cos(a) = \frac{s}{\sqrt{s^2+R^2}}, \quad (64a)$$

and $$b=\psi \quad (64b).$$

Hence, the Jacobian is:

$$\frac{\partial(\cos(a),b)}{\partial(s,\psi)} = \frac{R^2}{(s^2+R^2)^{3/2}}. \quad (64c)$$

Consequently:

$$Q_2(x,t) = \frac{-1}{4\pi^2}\int_{s/2}I(\theta,t)\delta'(<x-\phi(t),\theta>)d\theta, \quad (65)$$

which becomes:

$$\frac{-1}{4\pi^2}\int_0^\pi\int_{-\infty}^\infty\frac{R^2I(s,\psi,t)}{(s^2+R^2)^{3/2}}\delta'\left(\frac{Q_2(x,t)=}{\sqrt{u_x^2+v_x^2+R^2}\sqrt{s^2+R^2}}(u\cos\psi+v_x\sin\psi-s)\right). \quad (66)$$

After integrating with respect to s:

$$Q_2(x,t) = \quad (67)$$

$$\frac{(u_x^2+v_x^2+R^2)}{4\pi^2\|x-\phi(t)\|^2}\int_0^\pi\frac{\partial}{\partial s}\left[\frac{I(s,\psi,t)}{\sqrt{s^2+R^2}}\right]_{s=u_x\cos\psi+v_x\sin\psi}d\psi.$$

With particular reference to FIG. 6, the $Q_2$ calculation 50 is divided into four parts. First, a processor or means 60 computes line integrals of the weighted partial cone-beam data. This is followed by a processor or means 62 for estimating the partial derivative of the line integrals with respect to the variable s, which represents the distance from the origin $\Omega$ of the local coordinate system to the lines in accordance with Equation (54). The partial derivatives of the line integrals $H_t(s,\psi)$ are weighted by $(R^2+s^2)/(4\pi^2s^2)$. This weighting is inversely proportional to $\cos^2(a)$, where a denotes the divergence angle between the line $\phi(t)\Omega$ and the plane generated by the vertex $\phi(t)$ and the line parameterized by $(s,\psi)$. For simplicity of computation, the parallel beam geometry described by the parameters $(s,\psi)$ on the local coordinate plane is utilized throughout the computation of $Q_2$.

A second part 46 computes the weight W associated with each line $(s,\psi)$ in order to insure the normalization of the 3D backprojection when reconstructing the images. To insure this normalization, the number of intersections of a plane with the portion of the helix in which the data are three-dimensionally backprojected for reconstruction are computed for each plane defined by $(s,\psi)$. A processor or means 70 identifies the affected volume $V_r$. More specifically, a processor or means 72 computes the traces $A_z$ and $B_z$ of the end points of the backprojection range for each slice, indexed by c, in the affected volume $V_r$. A processor or means 74 computes the weighting function $W_t$ for each view t of each slice z in accordance with:

$$W_{tz}(s,\psi)=N_{tz}(s,\psi)|<\phi'(t),(s,\psi)>| \quad (68).$$

Due to the fact that the truncated data is not used in backprojection, a count of the number of intersection vertices with non-truncated data along the plane is also counted.

Figure 12:
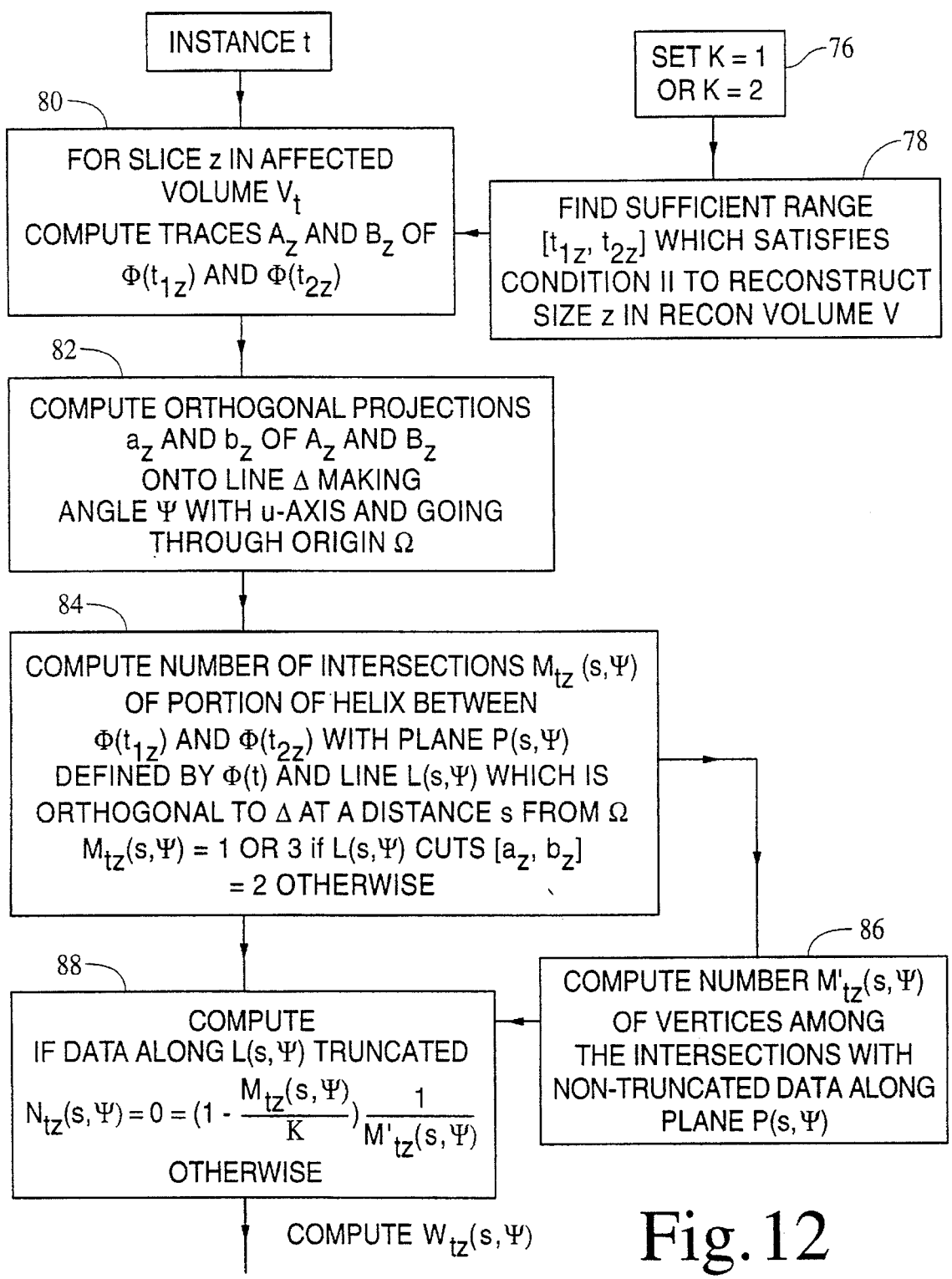
FIG. 12 further illustrates the reconstruction algorithm as shown in FIG. 6.

With reference to FIG. 12 and continuing reference to FIG. 6, without counting the current vertex $\phi(t)$, the number of intersections of a plane defined by the line $(s,\psi)$ is equal to the number of intersections of the line $(s,\psi)$ with the two branches of the trace of the portion of the helix in which the data are backprojected to create a slice of the reconstructed volume. This number is constant and equal to 1 when the line $(s,\psi)$ cuts the line $\Delta$ outside the line segment defined by the orthogonal projections of $\Delta$ of the traces of the two extreme vertices of the portion of the helix. Inside this line segment, the number is either 0 or 2. That is, the line $(s,\psi)$ either intersects the two branches of the trace or it does not have a common point with the trace at all. Second, because the weight is null for lines along which the data are truncated, it is not necessary to do any computation of line integrals or other related factors of these truncated lines.

More specifically, it is predetermined into how many slices the data is to be reconstructed, the number of pixels per slice, and the like. For each view t, a determination is made which slices are affected by view t, K is set 76 accordingly to either 1 or 2 for the reconstruction process. Once K is set, C from Equation (27) is known as is the weight of $Q_1$, which gives the range of each slice. At 78 a sufficient range $[t_{1z}, t_{2z}]$ which satisfies the condition 2, i.e., that the angle between the half lines Mu' and Md' is less than the angle between Mu' and $MI_1$ to reconstruct slice C in the reconstruction volume V. From the range, the weighting for $Q_2$ is determined. For each view t, a step or means 80 computes the traces $A_z$ and $B_z$ of $\phi(t_{1z})$ and $\phi(t_{2z})$ for each slice z in the affected volume $v_r$. A step or means 82 computes orthogonal projections $a_z$ and $b_z$ of the traces $A_z$ and $B_z$ onto the line $\Delta$ which makes an angle $\psi$ with the u-axis and goes through the origin $\Omega$.

With reference to FIGS. 6 and 12, a step or means 84 computes the number of intersections $M_{rz}(s,\psi)$ of the portion of the helix between $\psi(t_{1z})$ and $\psi(t_{2z})$ with the plane $P(s,\psi)$ defined by $\psi(t)$ and the line $L(s,\psi)$, which is orthogonal to the line $\Delta$ at a distance s from $\Omega$. Again, the helix can only intersect the plane at 1, 2, or 3 points. $M_{rz}(s,\psi)=1$ or 3, if the line L of $(s,\psi)$ cuts $[a_z, b_z]$. Otherwise, $M_{rz}(s,\psi)=2$. The step or means 86 computes the number $M'_{rz}(s,\psi)$ of the vertices among the intersections with non-truncated data along the plane $P(s,\psi)$. A step or means 88 computes the number $N_{rz}(s,\psi)$ which is supplied to the step or means 74 to compute the weighting function $W_{rz}(s,\psi)$. The number of intersections is calculated in accordance with:

$$N_{rz}(s, \psi)=0 \quad (69a),$$

if data along $L(s,\psi)$ is truncated, and $$N_{rz}(s,\psi) = \left(1 - \frac{M_{rz}(s,\psi)}{K}\right) \frac{1}{M'_{rz}(s,\psi)}, \quad (69b)$$

otherwise.

With reference again to FIG. 6, a processor 90 determines a partial derivative with respect to s and weights it. More specifically, a step or means 92 computes $I_{rz}(s,\psi)=W_{rz}(s,\psi) P_t(s,\psi)$. A step or means 94 determines the Jacobian $J_{rz}(s,\psi)$ as follows:

$$J_{rz}(s,\psi) = \frac{\partial}{\partial s} \frac{I_{rz}(s,\psi)}{\sqrt{s^2 + R^2}}. \quad (70)$$

A processor 96 multiplies, at each pixel (u,v) in the local coordinate plane, the backprojection of (u,v) from the processor 90 with the square of the distance from the vertex $\phi(t)$ to the pixel. More specifically, a step or means 98 adds up 180° of parallel beam backprojections. It performs a parallel beam two-dimensional backprojection of $J_{rz}$ at each (u,v) to compute $B_{rz}(u,v)$. A step or means 100 computes $Q_{2rz}(u,v) =(u^2+v^2+R^2)B_{rz}(u,v)$. These values of $Q_2$ are supplied to the summation means 52 to be combined with the corresponding values of $Q_1$.

Figure 13:
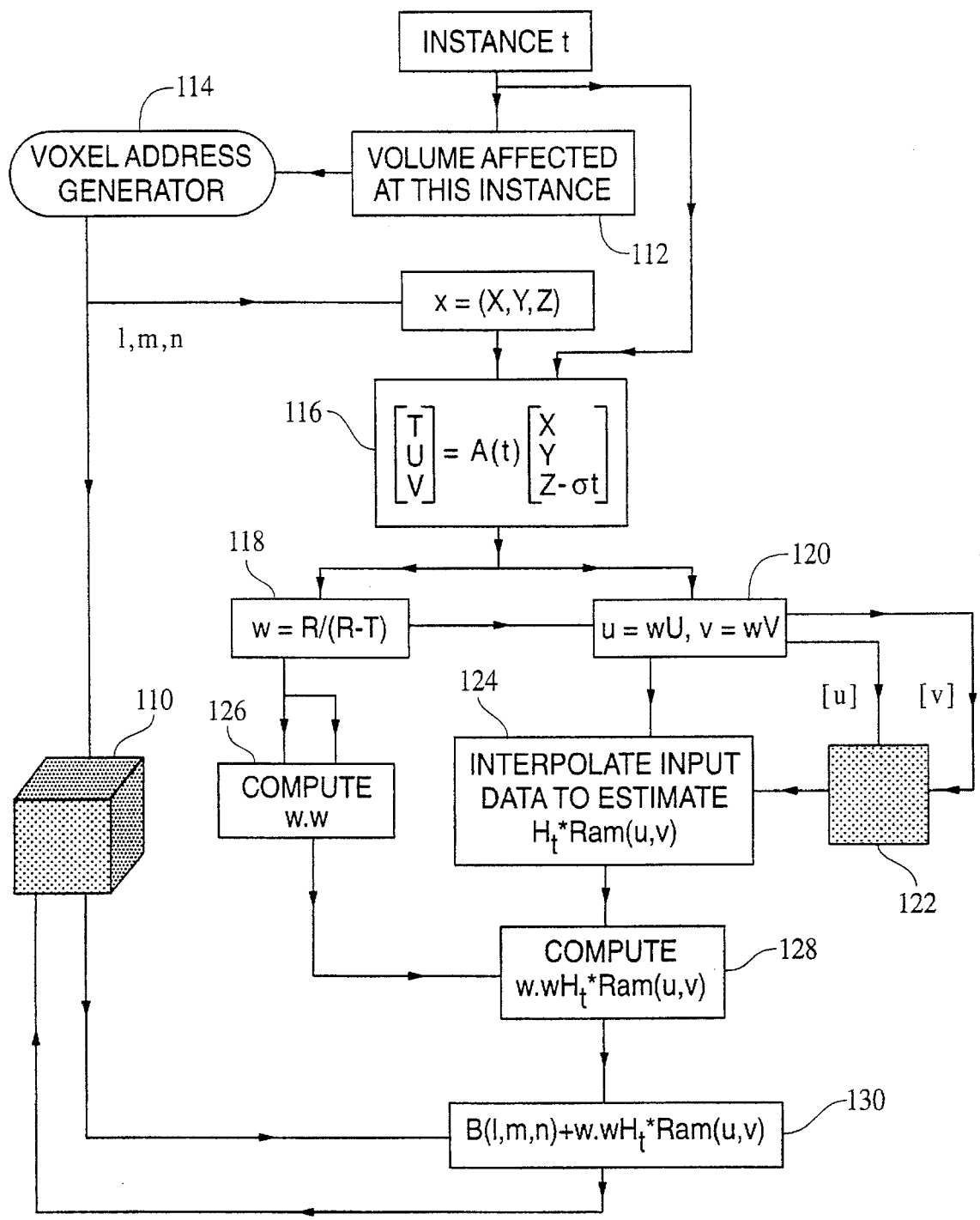
FIG. 13 illustrates the backprojection process.
Figure 14:
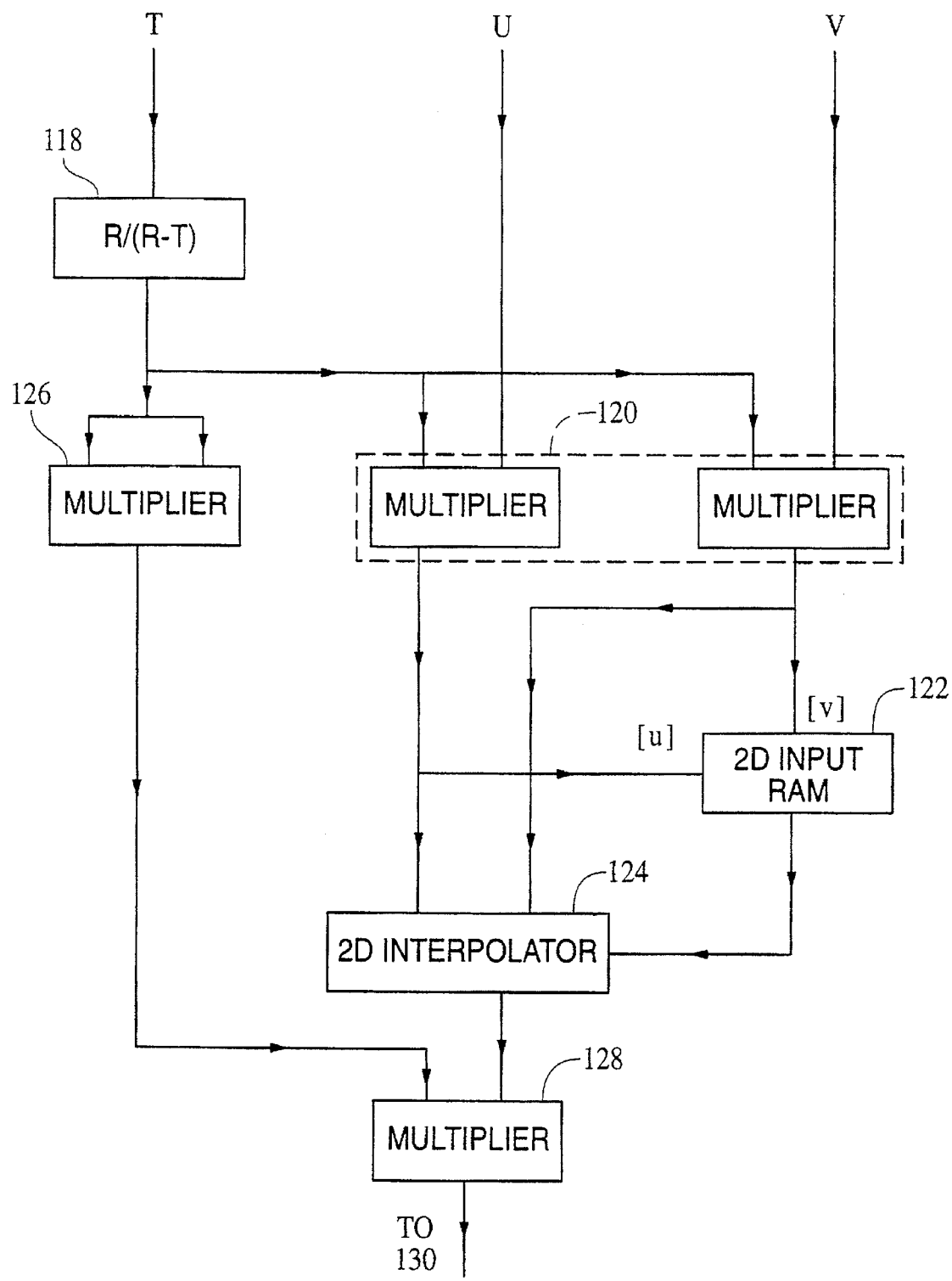
FIG. 14 is a detailed view illustrating the processing of three-dimensional data for projection into a three-dimensional region of the volume image memory.

With reference to FIGS. 13 and 14, the three-dimensional backprojector 54 is a processor which computes the final reconstruction from the processed data, such as the above-described convolved data. The backprojector is an estimator of:

$$f(x) = \int_{\Lambda_x} Q(x,t)dt, \quad (71)$$

where Q represents the processed data. Because the data are collected at only a finite number of instances, the integral can be approximated by the finite sum:

$$f(x) = \Delta t \Sigma Q(x, t_i) \quad (72),$$

Further, the continuous volume can be represented by a finite number of voxels of size $\Delta X \Delta Y \Delta Z$, that is $x=(l\Delta X, m\Delta Y, n\Delta Z)+(X_0, Y_0, Z_0)$ for some $l=0, 1, \ldots, L-1, m=0, 1, \ldots, M-1, n=0, 1, \ldots, N-1$. $(X_0,Y_0,Z_0)$ is a corner of the represented volume.

When Q is reduced to $Q_1$, then Q is estimated by appropriately weighting the convolved data $H_r$. Due to the fact that at each instance t, data are collected only along a finite number of rays within a partial cone-beam, $H_t(u,v)$ must be approximated from a sample $\{H_t(i\Delta u+u_0, j\Delta v+v_0) | i=0, 1, \ldots, I-1, \text{ and } j=0, 1, \ldots, J-1\}$. It should further be noted that because there is data within a partial cone geometry, the backprojection of the processed data does not affect the whole represented volume, but only a portion of it. Another important point is that the backprojection is conveniently carried out in a new coordinate system defined by (C(t),U,V).

With particular reference to FIG. 13, a three-dimensional image memory 110 receives the backprojected views. As each view t is received, an affected volume determining means or step 112 determines the part of the volume of memory 110 which is affected by the processed view t. A voxel generator 114 sweeps through all of the voxels in the affected part of the volume. A coordinate transform processor 116 converts the absolute coordinate system (X,Y,Z) of the voxel address generator into the local coordinate system (T,U,V). With continuing reference to FIG. 13 and further reference to FIG. 14, a weight generating system includes a first weight generator 118 which generates a first weighting value w which is equal to R/(R−T). A two-dimensional input generator 120 which generates local coordinates of a voxel given by the voxel generator, the local address being (u,v) and generates weighting factors u and w, where u=wU and v=wV. The u and v addresses address a two-dimensional memory 122 in which the two-dimensional view $H_t$*RAM is stored. An input interpolator 124 uses the input data retrieved from the input memory 122 and fractional parts of the new coordinates calculated by the two-dimensional input generator 120 to estimate the input data corresponding to a ray going through the voxel given by the voxel generator. A multiplier 126 multiplies the weighting factor w by itself to form a weighting factor $w^2$. A multiplier 128 multiplies the interpolated input data $H_t$*RAM(u,v) by the squared weighting function $w^2$. An adder 130 retrieves the current values B(l,m,n) retrieved from the volumetric memory 110 with the product from the multiplier 128. In this manner, the values stored in each voxel is updated with each two-dimensional set of processed data. Initially, the three-dimensional output memory 110 has each pixel value assigned a nominal, non-zero starting value, e.g., 1. In this manner, the value at each voxel is iteratively updated until an accurate reconstruction is obtained.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A radiographic diagnostic apparatus comprising:

a source of penetrating radiation;

a two-dimensional radiation detector for receiving partial cone-beam radiation along a plurality of divergent rays, the rays being focused at a common origin vertex and diverging in two dimensions; the radiation detector, the source, and a subject support being disposed to irradiate a subject on the support along at least a helical arc segment of a helical path;

a means for sampling the radiation detector at a plurality of angular increments along the helical arc segment to generate a plurality of two-dimensional views, each view including a two-dimensional array of data values, each data value corresponding to one of the divergent rays, data along rows parallel to a tangent to the helical arc segment at the vertex being untruncated and data in at least one-direction not parallel to the tangent being truncated;

a weighting processor for weighting the data values of each two-dimensional array in accordance with a cosine of an angle between a ray corresponding to the data value and a ray normal to a local coordinate plane at the radiation detector;

a first component processor for convolving a first component of the weighted data values one-dimensionally parallel to the tangent to create a convolved first two-dimensional data component array;

a second component processor for processing a second two-dimensional component array of the weighted data values, the second processor weights each second component value in accordance with characteristics of the helical arc segment and position along the helical arc segment, for taking a partial derivative of the data values of the second component, and for multiplying each data value in accordance with a square of a distance from the vertex of the divergent rays to the radiation detector corresponding to each data value;

an adder for combining the first and second processed components from the first and second component processors; and, a backprojector for three-dimensionally backprojecting the sum from the adder into a volumetric image memory.

2. The scanner as set forth in claim 1 wherein the second component processor includes:

a means for computing a line integral of the weighted data;

a means for computing a cosine weighted first derivative of the line integral;

a means for computing a product of the cosine weighted line integral and a weighting function;

a means for computing a partial derivative of the product;

a means for backprojecting the partial derivative to generate a backprojection; and, a means for weighting the backprojection to form the processed second two-dimensional component array.

3. The scanner as set forth in claim 2 further including a means for generating the weighting function, the weighting function generating means including:

a means for determining a sub-volume of the volumetric image memory affected by each two-dimensional array; and, a means for computing traces of end points of the backprojection range for each slice within the volumetric memory, and a means for multiplying a second weighting value based on the trace to generate the weighting function.

4. The scanner as set forth in claim 3 further including:

a means for generating the second weighting value, the second weighting value generating means including a means for computing orthogonal projections of the traces;

a means for computing a number of intersections between the helical arc segment and a plane defined by the first derivative of the line integral;

a means for determining a number of times that the plane intersects the helical arc segment;

a means for determining intersections of vertices with non-truncated data along the plane; and, a means for setting the weighting function to zero for truncated data and for setting the weighting function equal to a value which is proportional to 1 minus the number of intersections divided by a constant and weighted by an inverse of a number of vertices among the intersections with non-truncated data to generate the second weighting value.

5. The scanner as set forth in claim 1 wherein the backprojector includes:

a means for determining a volumetric segment of the volumetric image memory affected by each two-dimensional backprojected data set;

a voxel address generator for generating addresses for the volumetric image memory corresponding to the affected volume;

a coordinate transform means for coordinating a coordinate system of the volumetric image memory and each two-dimensional data set;

a means for addressing the two-dimensional data set to retrieve data values corresponding to each address generated by the address generator;

a weighting means for weighting each retrieved data value from the two-dimensional data set; and, a means for retrieving a stored data value from the volumetric memory corresponding to each address generated by the voxel address generator and adding the corresponding weighted data value from the two-dimensional data set thereto.

6. The scanner as set forth in claim 5 further including an interpolator for interpolating each data value from the two-dimensional data set to correct for fractional addresses generated by transforming from the voxel generator address to the coordinate system of each two-dimensional data set.

7. A method for radiographic diagnostic imaging comprising:

generating penetrating radiation;

receiving the radiation with a two-dimensional radiation detector along a plurality of divergent rays, the rays being focused at a common origin vertex and diverging in two dimensions;

rotating the vertex along at least an arc segment of a helical path;

sampling the radiation detector at a plurality of angular increments along the helical arc segment to generate a plurality of two-dimensional views, each view including a two-dimensional array of data values, each data value corresponding to one of the divergent rays, the data values along rows parallel to a tangent to the arc segment at the vertex being untruncated and the data values in at least one other direction being truncated;

weighting the data values of each two-dimensional array in accordance with a cosine of an angle between a ray corresponding to the data value and a ray normal to a local coordinate plane at the radiation detector;

convolving a first component of the weighted data values one-dimensionally parallel to the tangent to create a convolved first two-dimensional data component array;

processing a second two-dimensional component array of the weighted data, each second component value being weighted in accordance with characteristics of the helical arc segment and position along the helical arc segment, taking a partial derivative of the data values of the second component, and multiplying each data value in accordance with a square of a distance from the vertex of the divergent rays to the radiation detector corresponding to each data value;

combining the first and second processed components; and, three-dimensionally backprojecting the sum into a volumetric image memory.

8. The method as set forth in claim 7 wherein the processing includes:

computing a line integral of the weighted data;

computing a cosine weighted first derivative of the line integral;

computing a product of the cosine weighted line integral and a weighting function;

computing a partial derivative of the product;

backprojecting the partial derivative to generate a backprojection; and, weighting the backprojection to form the processed second two-dimensional component array.

9. The method as set forth in claim 8 further including generating the weighting function, the generating including:

determining a sub-volume of the volumetric image memory affected by each two-dimensional array; and, computing traces of end points of the backprojection range for each slice within the volumetric memory, and a means for multiplying by a second weighting value based on the trace to generate the weighting function.

10. The method as set forth in claim 9 further including generating the second weighting value, the generating including computing orthogonal projections of the traces;

computing a number of intersections between the helical arc segment and a plane defined by the first derivative of the line integral;

determining a number of times that the plane intersects the helical arc segment;

determining intersections of vertices with non-truncated data along the plane; and, setting the weighting function to zero for truncated data and for setting the weighting function equal to a value which is proportional to 1 minus the number of intersections divided by a constant and weighted by an inverse of a number of vertices among the intersections with non-truncated data to generate the second weighting value.

11. The method as set forth in claim 7 wherein the backprojecting includes:

determining a volumetric segment of the volumetric memory affected by each two-dimensional backprojected data set;

generating voxel addresses for the three-dimensional volumetric memory corresponding to the affected volume;

coordinating a coordinate system of the volumetric image memory and each two-dimensional data set;

addressing the two-dimensional data set to retrieve data values corresponding to each voxel address generated;

weighting each retrieved data value from the two-dimensional data set; and, retrieving a stored data value from the volume memory corresponding to each voxel address generated and adding the corresponding weighted data value from the two-dimensional data set thereto.

12. The scanner as set forth in claim 11 further including interpolating each data value from the two-dimensional data set to correct for fractional addresses generated by transforming from the voxel address to the coordinate system of each two-dimensional data set array.

13. In a method of diagnostic imaging in which a vertex of a cone-beam of radiation moves along a helical trajectory, which cone-beam of radiation passes through a subject and is converted to a plurality of two-dimensional views of data values, the improvement comprising:

collecting partial cone beam views which are untruncated in a direction which is parallel to a tangent to the trajectory at the vertex and which are truncated in another direction;

reconstructing the views into a volumetric image representation using an exact reconstruction algorithm.

14. In a method of diagnostic imaging in which a vertex of a cone-beam of radiation moves along a helical trajectory, which cone-beam of radiation passes through a subject and is converted to a plurality of two-dimensional views of data values, the improvement comprising:

collecting partial cone beam views which are untruncated in a direction which is parallel to a tangent to the trajectory at the vertex and which are truncated in another direction;

defining planes and voxel locations of a three-dimensional volumetric image representation;

reconstructing the views based on the defined planes and voxel locations such that views contribute to multiple planes to generate a three-dimensional diagnostic image representation.

15. In a method of diagnostic imaging in which diagnostic data views are reconstructed and backprojected to construct a volumetric image representation, the improvement comprising:

collecting partial cone-beam views which are truncated in one direction, the partial cone-beam moving along a spiral;

backprojecting each partial cone-beam view into a three-dimensional portion f the volumetric image representation such that each backprojected partial cone-beam view contributes to a plurality of parallel planes of a part of the volumetric image representation in accordance with an intersection of the partial cone-beam and the parallel planes.

* * * * *